(12) United States Patent
Moore et al.

(10) Patent No.: US 6,265,560 B1
(45) Date of Patent: Jul. 24, 2001

(54) HUMAN STE20-LIKE STRESS ACTIVATED SERINE/THREONINE KINASE

(75) Inventors: William Craig Moore, West Grove, PA (US); Tyrrell Errick Norris, New Castle, DE (US); David Shay Silberstein, Kennett Square, PA (US)

(73) Assignee: Zeneca Ltd. (GB)

( * ) Notice: Subject to any disclaimer, the term of this patent is extended or adjusted under 35 U.S.C. 154(b) by 0 days.

(21) Appl. No.: 09/152,406

(22) Filed: Sep. 14, 1998

(30) Foreign Application Priority Data

Sep. 19, 1997 (GB) ................................. 9719920

(51) Int. Cl.[7] .......................... C12N 15/54; C07M 21/00
(52) U.S. Cl. ......................... 536/23.2; 536/23.5
(58) Field of Search .......................... 435/29, 69.1, 91.1, 435/320.1, 325, 373, 375, 455; 536/23.1, 23.2, 23.4, 23.5

(56) References Cited

FOREIGN PATENT DOCUMENTS

WO97/42212   11/1997   (GB) .

OTHER PUBLICATIONS

Pombo, Celia M. et al., Activation of a human Ste20–like kinase byOxidant Stress Defines a Novel Stress Response Pathway, The Embo Journal, 15/17:4537 (1996).
Friedemann Kiefer [1,2], et al., HPK1, A Hematopoietic Protein Kinase Activating the SAPK/JNK Pathway, The Embo Journal, 15/24:7013 (1996).
Creasy, Caretha L., et al., Cloning and Characterization of a Member of the MST Subfamily of Ste20–Like Kinases, Gene, 167:303 (1995).
Hu, Mickey C.–T., et al., Human HPK1, A Novel Human Hematopoietic Progenitor Kinase That Activates the JNK/SAPK Kinase Cascade, Genes and Development, 10:2251 (1996).
Creasy, Caretha L., et al., Cloning and Characterization of a Human Protein Kinase with Homology to Ste20, The Journal of Biological Chemistry, 270:21695 (1995).
Pombo, Cella M. et al., Activation of the SAPK Pathway by the Human STE20 Homologue Germinal Centre Kinase, Nature, 377:750 (1995).
Creasy, Caretha L., et al., The Ste20–like Protein Kinase, Mst1, Dimerizes and Contains and Inhibitory Domain, The Journal of Biological Chemistry, 271:21049 (1996).
Hanks, Steven K., et al., Protein Kinases 6—The Eukaryotic Protein Kinase Superfamily: Kinase (Catalytic) Domain Structure and Classification[1], The FASEB Journal, 9:578 (1995).
Hanks, Steven K., et al., The Protein Kinase Family: Conserved Features and Deduced Phylogeny of the Catalytic Domains, Science 241:42 (1988).
Kyriakis, John M., et al., The Stress–Activated Protein Kinases, Annals New York Academy of Sciences, 766:303 (1995).
Grunicke, Hans H., et al., Signal Transduction Mechanisms in Cancer, Molecular Biology Intelligence Unit, p. 16, (1995).
Storz, G., et al., Transcriptional Regulators of Oxidative Stress–Inductive Genes in Prokaryotes and Eukaryotes, Stress–Inducible Cellular Responses, p. 239 (1996).
Ravichandran, K.S., et al., Coreceptor and Adapter Proteins in T–Cell Signaling, Annals of the New York Academy of Sciences, p. 117 (1995).
Tonks, N.K., Protein Tyrosine Phosphatases and the Control of Cellular Signaling Responses, Advances in Pharmacology, 36:91 (1996).
Polla, B. S., et al., Stress Proteins in Inflammation, Stress Inducible Cellular Responses, p. 375 (1996).
Cobb, Melanie H., et al., Structural Analysis of the MAP Kinase ERK2 and Studies of MAP Kinase Regulatory Pathways, Advances in Pharmacology, 16:49 (1996).
Moriguchi, Tetsuo, et al., Roles of the MAP Kinase Cascade in Vertebrates, Advances in Pharmacology, 36:121 (1996).
Cohen, Philip, Dissection of Protein Kinase Cascades That Mediate Cellular Response to Cytokines and Cellular Stress, Advances in Pharmacology, 36:15 (1996).
Welch, William J., et al., The Stress Response and the Immune System, Inflammation : Basic Principles and Clinical Correlates 41:841 (1992).
Excerpt from Regulation of Macrophage Function, Macrophages in Host Defense, p. 651 (1992).
Hanahan, Douglas, Signaling Vascular Morphogenesis and Maintenance, Science 277:48 (1997).
Holbrook, N.J., et al. Signaling Events Controlling the Molecular Response to Genotoxic Stress, Stress Inducible Cellular Responses, 273 (1996).
Schinkmann, K., et al., Cloning and Characterization of a Human STE20–like Protein Kinase with Unusyual Cofactor Requirements, J. Biol. Chem., 272(45):28695 (1997).
GENBANK Publication, Locus AFO24636, PRI Nov. 2, 1997.

*Primary Examiner*—Robert A. Schwartzman
*Assistant Examiner*—Thomas G. Larson
(74) *Attorney, Agent, or Firm*—Kenneth F. Mitchell

(57) ABSTRACT

A novel human signal-transduction kinase polypeptide is described which is expressed at a particularly high level in human leukocytes. A full length cDNA which encodes the novel stress-activated serine/threonine kinase polypeptide is disclosed as well as the interior structural region and the amino acid residue sequence of the native biological molecule. Methods are provided to identify compounds that modulate the biological activity of the human Ste20-like stress-activated serine/threonine signal transduction kinase.

1 Claim, 10 Drawing Sheets

5' GAGCGCCATGGCTCACTCCCCGGTGCAGTCGGGCCTGCCCGGCATGCAGAACCTAAAGGCAGACCCAGAAGAGCTTTTA
CAAAACTAGAGAAAATTGGGAAGGGCTCCTTTGGAGAGGTGTTCAAAGGCATTGACAATCGGACTCAGAAAGTGGTTGCC
ATAAAGATCATTGATCTGGAAGAAGCTGAAGATGAGATAGAGGACATTCAACAAGAAATCACAGTGCTGAGTCAGTGTGA
CAGTCCATATGTAACCAAATATTATGGATCCTATCTGAAGGATACAAAATTATGGATAATAATGGAATATCTTGGTGGAG
GCTCCGCACTAGATCTATTAGAACCTGGCCCATTAGATGAAACCCAGATCGCTACTATATTAAGAGAAATACTGAAAGGA
CTCGATTATCTCCATTCGGAGAAGAAAATCCACAGAGACATTAAAGCGGCCAACGTCCTGCTGTCTGAGCATGGCGAGGT
GAAGCTGGCGGACTTTGGCGTGGCTGGCCAGCTGACAGACACCCAGATCAAAAGGAACACCTTCGTGGGCACCCCATTCT
GGATGGCACCCGAGGTCATCAAACAGTCGGCCTATGACTCGAAGGCAGACATCTGGTCCCTGGGCATAACAGCTATTGAA
CTTGCAAGAGGGGAACCACCTCATTCCGAGCTGCACCCCATGAAAGTTTTATTCCTCATTCCAAAGAACAACCCACCGAC
GTTGGAAGGAAACTACAGTAAACCCCTCAAGGAGTTTGTGGAGGCCTGTTTGAATAAGGAGCCGAGCTTTAGACCCACTG
CTAAGGAGTTATTGAAGCACAAGTTTATACTACGCAATGCAAAGAAAACTTCCTACTTGACCGAGCTCATCGACAGGTAC
AAGAGATGGAAGGCCGAGCAGAGCCATGACGACTCGAGCTCCGAGGATTCCGACGCGGAAACAGATGGCCAAGCCTCGGG
GGGCAGTGATTCTGGGGACTGGATCTTCACAATCCGAGAAAAAGATCCCAAGAATCTCGAGAATGGAGCTCTTCAGCCAT
CGGACTTGGACAGAAATAAGATGAAAGACATCCCAAAGAGGCCTTTCTCTCAGTGTTTATCTACAATTATTTCTCCTCTG
TTTGCAGAGTTGAAGGAGAAGAGCCAGGCGTGCGGAGGGAACTTGGGGTCCATTGAAGAGCTGCGAGGGGCCATCTACCT
AGCGGAGGAGGCGTGCCCTGGCATCTCCGACACCATGGTGGCCCAGCTCGTGCAGCGGCTCCAGAGATACTCTCTAAGTG
GTGGAGGAACTTCATCCCACTGAAATTCCTTTGGCATTTGGGGTTTTGTTTTTCCTTTTTTCCTTCTTCATCCTCCTCCT
TTTTTAAAAGTCAACGAGAGCCTTCGCTGACTCCACCGAAGAGGTGCGCCACTGGGAGCCACCCCAGCGCCAGGCGCCCG
TCCAGGGACACACACAGTCTTCACTGTGCTGCAGCCAGATGAAGTCTCTCAGATGGGTGGGAGGGTCAGCTCCTTCCAG
CGATCATTTTATTTTATTTTATTACTTTTGTTTTTAATTTTAACCATAGTGCACATATTCCAGGAAAGTGTCTTTAAAAA
CAAAAACAAACCCTGAAATGTATATTTGGGATTATGATAAGGCAACTAAAGACATGAAACCTCAGGTATCCTGCTTTAAG
TTGATAACTCCCTCTGGGAGCTGGAGAATCGCTCTGGTGGATGGGTGTACAGATTTGTATATAATGTCATTTTTACGGAA
ACCCTTTCGGCGTGCATAAGGAATCACTGTGTACAAACTGGCCAAGTGCTTCTGTAGATAACGTCAGTGGAGTAAATATT
CGACAGGCCATAACTTGAGTCTATTGCCTTGCCTTTATTACATGTACATTTTGAATTCTGTGACCAGTGATTTGGGTTTT
ATTTTGTATTTGCAGGGTTTGTCATTAATAATTAATGCCCCTCTCTTACAGAACACTCCTATTTGTACCTCAACAAATGC
AAATTTTCCCCGTTTGCCCTACGCCCCTTTTGGTACACCTAGAGGTTGATTTCCTTTTTCATCGATGGTACTATTTCTTA
GTGTTTTAAATTGGAACATATCTTGCCTCATGAAGCTTTAAATTATAATTTTCAGTTTCTCCCCATGAAGCGCTCTCGTC
TGACATTTGTTTGGAATCGTGCCACTGCTGGTCTGCGCCAGATGTACCGTCCTTTCCAATACGATTTTCTGTTGCACCTT
GTAGTGGATTCTGCATATCATCTTTCCCACCTAAAAATGTCTGAATGCTTACACAAATAAATTTTATAACACGCTTAAAA
AA 3'

FIG. 1

5' ATGGCTCACTCCCCGGTGCAGTCGGGCCTGCCCGGCATGCAGAACCTAAAGGCAGACCCAGAAGAGCTTTTTACAAAACT
AGAGAAAATTGGGAAGGGCTCCTTTGGAGAGGTGTTCAAAGGCATTGACAATCGGACTCAGAAAGTGGTTGCCATAAAGA
TCATTGATCTGGAAGAAGCTGAAGATGAGATAGAGGACATTCAACAAGAAATCACAGTGCTGAGTCAGTGTGACAGTCCA
TATGTAACCAAATATTATGGATCCTATCTGAAGGATACAAAATTATGGATAATAATGGAATATCTTGGTGGAGGCTCCGC
ACTAGATCTATTAGAACCTGGCCCATTAGATGAAACCCAGATCGCTACTATATTAAGAGAAATACTGAAAGGACTCGATT
ATCTCCATTCGGAGAAGAAAATCCACAGAGACATTAAAGCGGCCAACGTCCTGCTGTCTGAGCATGGCGAGGTGAAGCTG
GCGGACTTTGGCGTGGCTGGCCAGCTGACAGACACCCAGATCAAAAGGAACACCTTCGTGGGCACCCCATTCTGGATGGC
ACCCGAGGTCATCAAACAGTCGGCCTATGACTCGAAGGCAGACATCTGGTCCCTGGGCATAACAGCTATTGAACTTGCAA
GAGGGGAACCACCTCATTCCGAGCTGCACCCCATGAAAGTTTTATTCCTCATTCCAAAGAACAACCCACCGACGTTGGAA
GGAAACTACAGTAAACCCCTCAAGGAGTTTGTGGAGGCCTGTTTGAATAAGGAGCCGAGCTTTAGACCCACTGCTAAGGA
GTTATTGAAGCACAAGTTTATACTACGCAATGCAAAGAAAACTTCCTACTTGACCGAGCTCATCGACAGGTACAAGAGAT
GGAAGGCCGAGCAGAGCCATGACGACTCGAGCTCCGAGGATTCCGACGCGGAAACAGATGGCCAAGCCTCGGGGGGCAGT
GATTCTGGGGACTGGATCTTCACAATCCGAGAAAAAGATCCCAAGAATCTCGAGAATGGAGCTCTTCAGCCATCGGACTT
GGACAGAAATAAGATGAAAGACATCCCAAAGAGGCCTTTCTCTCAGTGTTTATCTACAATTATTTCTCCTCTGTTTGCAG
AGTTGAAGGAGAAGAGCCAGGCGTGCGGAGGGAACTTGGGGTCCATTGAAGAGCTGCGAGGGGCCATCTACCTAGCGGAG
GAGGCGTGCCCTGGCATCTCCGACACCATGGTGGCCCAGCTCGTGCAGCGGCTCCAGAGATACTCTCTAAGTGGTGGAGG
AACTTCATCCCACTGA 3'

FIG. 2

MAHSPVQSGLPGMQNLKADPEELFTKLEKIGKGSFGEVFKGIDNRTQKVVAIKIIDLEEAEDEIEDIQQEITVLSQCDSP
YVTKYYGSYLKDTKLWIIMEYLGGGSALDLLEPGPLDETQIATILREILKGLDYLHSEKKIHRDIKAANVLLSEHGEVKL
ADFGVAGQLTDTQIKRNTFVGTPFWMAPEVIKQSAYDSKADIWSLGITAIELARGEPPHSELHPMKVLFLIPKNNPPTLE
GNYSKPLKEFVEACLNKEPSFRPTAKELLKHKFILRNAKKTSYLTELIDRYKRWKAEQSHDDSSSEDSDAETDGQASGGS
DSGDWIFTIREKDPKNLENGALQPSDLDRNKMKDIPKRPFSQCLSTIISPLFAELKEKSQACGGNLGSIEELRGAIYLAE
EACPGISDTMVAQLVQRLQRYSLSGGGTSSH

FIG. 3

MAHLRGFANQHSRVDPEELFTKLDRIGKGSFGEVYKGIDNHTKEVVAIKIIDLEEAEDEIEDIQQEITVLSQCDSPYITR
YFGSYLKSTKLWIIMEYLGGGSALDLLKPGPLEETYIATILREILKGLDYLHSERKIHRDIKAANVLLSEQGDVKLADFG
VAGQLTDTQIKRNTFVGTPFWMAPEVIKQSAYDFKADIWSLGITAIELAKGEPPNSDLHPMRVLFLIPKNSPPTLEGQHS
KPFKEFVEACLNKDPRFRPTAKELLKHKFITRYTKKTSFLTELIDRYKRWKSEGHGEESSSEDSDIDGEAEDGEQGPIWT
FPPTIRPSPHSKLHKGTALHSSQKPADAVKRQPRSQCLSTLVRPVFGELKEKHKQSGGSVGALEELENAFSLAEESCPGI
SDKLMVHLVERVQRFSHNRNHLTSTR

5' TTTTTTAAGCGTGTTATAAAATTTATTTGTGTAAGCATTCAGACATTTTTAGGTGGGAAAGATGATATGCAGAATCCACT
ACAAGGTGCAACAGAAAATCGTATTGGAAAGGACGGTACATCTGGCGCAGACCAGCAGTGGCACGATTCCAAACAAATGT
CAGACGAGAGCGCTTCATGGGGAGAAACTGAAAATTATAATTTAAAGCTTCATGAGGCAAGATATGTTCCAATTTAAAAC
ACTAAGAAATAGTACCATCGATGAAAAGGAAATCAACCTCTAGGTGTACCAAAAGGGGCGTAGGGCAAACGGGGAAAAT
TTGCATTTGTTGAGGTACAAATAGGAGTGTTCTGTAAGAGAGGGGCATTAATTATTAATGACAAACCCTGCAAATACAAA
ATAAAACCCAAATCACTGGTCACAGAATTCAAAATGTACATGTAATAAAGGCAAGGCAATAGACTCAAGTTATGGCCTGT
CGAATATTTACTCCACTGACGTTATCTACAGAAGCACTTGGCCAGTTTGTACACAGTGATTCCTTATGCACGCCGAAAGG
GTTTCCGTAAAAATGACATTATATACAAATCTGTACACCCATCCACCAGAGCGATTCTCCAGCTCCCAGAGGGAGTTATC
AACTTAAAGCAGGATACCTGAGGTTTCATGTCTTTAGTTGCCTTATCATAATCCCAAATATACATTTCAGGGTTTGTTTT
TGTTTTTAAAGACACTTTCCTGGAATATGTGCACTATGGTTAAAATTAAAAACAAAAGTAATAAAATAAAATAAAATGAT
CGCTGGAAGGAGCTGACCCTCCCCACCCATCTGAGAGACTTCATCTGGCTGCAGCACAGTGAAGACTGTGTGTGTCCCTG
GACGGGCGCCTGGCGCTGGGGTGGCTCCCAGTGGCGCACCTCTTCGGTGGAGTCAGCGAAGGCTCTCGTTGACTTTTAAA
AAAGGAGGAGGATGAAGAAGGAAAAAAGGAAAAACAAAACCCCAAATGCCAAAGGAATTTCAGTGGGATGAAGTTCCTCC
ACCACTTAGAGAGTATCTCTGGAGCCGCTGCACGAGCTGGGCCACCATGGTGTCGGAGATGCCAGGGCACGCCTCCTCCG
CTAGGTAGATGGCCCCTCGCAGCTCTTCAATGGACCCCAAGTTCCCTCCGCACGCCTGGCTCTTCTCCTTCAACTCTGCA
AACAGAGGAGAAATAATTGTAGATAAACACTGAGAGAAAGGCCTCTTTGGGATGTCTTTCATCTTATTTCTGTCCAAGTC
CGATGGCTGAAGAGCTCCATTCTCGAGATTCTTGGGATCTTTTTCTCGGATTGTGAAGATCCAGTCCCCAGAATCACTGC
CCCCCGAGGCTTGGCCATCTGTTTCCGCGTCGGAATCCTCGGAGCTCGAGTCGTCATGGCTCTGCTCGGCCTTCCATCTC
TTGTACCTGTCGATGAGCTCGGTCAAGTAGGAAGTTTTCTTTGCATTGCGTAGTATAAACTTGTGCTTCAATAACTCCTT
AGCAGTGGGTCTAAAGCTCGGCTCCTTATTCAAACAGGCCTCCACAAACTCCTTGAGGGGTTTACTGTAGTTTCCTTCCA
ACGTCGGTGGGTTGTTCTTTGGAATGAGGAATAAAACTTTCATGGGGTGCAGCTCGGAATGAGGTGGTTCCCCTCTTGCA
AGTTCAATAGCTGTTATGCCCAGGGACCAGATGTCTGCCTTCGAGTCATAGGCCGACTGTTTGATGACCTCGGGTGCCAT
CCAGAATGGGGTGCCCACGAAGGTGTTCCTTTTGATCTGGGTGTCTGTCAGCTGGCCAGCCACGCCAAAGTCCGCCAGCT
TCACCTCGCCATGCTCAGACAGCAGGACGTTGGCCGCTTTAATGTCTCTGTGGATTTTCTTCTCCGAATGGAGATAATCG
AGTCCTTTCAGTATTTCTCTTAATATAGTAGCGATCTGGGTTTCATCTAATGGGCCAGGTTCTAATAGATCTAGTGCGGA
GCCTCCACCAAGATATTCCATTATTATCCATAATTTTGTATCCTTCAGATAGGATCCATAATATTTGGTTACATATGGAC
TGTCACACTGACTCAGCACTGTGATTTCTTGTTGAATGTCCTCTATCTCATCTTCAGCTTCTTCCAGATCAATGATCTTT
ATGGCAACCACTTTCTGAGTCCGATTGTCAATGCCTTTGAACACCTCTCCAAAGGAGCCCTTCCCAATTTTCTCTAGTTT
TGTAAAAAGCTCTTCTGGGTCTGCCTTTAGGTTCTGCATGCCGGGCAGGCCCGACTGCACCGGGGAGTGAGCCATGGCGC
TC 3'

FIG. 7

5' GGACTCAGAAAGTGGTTGCCATTCGAATAATTGATCTGGAAGAAGC 3'

SEQ ID NO:6

5' GCTTCTTCCAGATCAATTATTCGAATGGCAACCACTTTCTGAGTCC 3'

SEQ ID NO:7

FIG. 8

5' GAGCGCCATGGCTCACTCC 3'

SEQ ID NO:8

5' GGAGTCAGCGAAGGCTCTCG 3'

SEQ ID NO:9

FIG. 10

SEQUENCE LISTING

<160> NUMBER OF SEQ ID NOS: 9

<210> SEQ ID NO 1
<211> LENGTH: 2322
<212> TYPE: DNA
<213> ORGANISM: Homo Sapiens

<400> SEQUENCE: 1

| | | | | | |
|---|---|---|---|---|---|
| gagcgccatg | gctcactccc | cggtgcagtc | gggcctgccc | ggcatgcaga | acctaaaggc | 60 |
| agacccagaa | gagcttttta | caaaactaga | gaaaattggg | aagggctcct | ttggagaggt | 120 |
| gttcaaaggc | attgacaatc | ggactcagaa | agtggttgcc | ataaagatca | ttgatctgga | 180 |
| agaagctgaa | gatgagatag | aggacattca | acaagaaatc | acagtgctga | gtcagtgtga | 240 |

```
cagtccatat gtaaccaaat attatggatc ctatctgaag gatacaaaat tatggataat    300
aatggaatat cttggtggag gctccgcact agatctatta gaacctggcc cattagatga    360
aacccagatc gctactatat taagagaaat actgaaagga ctcgattatc tccattcgga    420
gaagaaaatc cacagagaca ttaaagcggc aacgtcctg ctgtctgagc atggcgaggt     480
gaagctggcg gactttggcg tggctggcca gctgacagac acccagatca aaggaacac     540 cttcgtgggc acccattct ggatggcacc cgaggtcatc aaacagtcgg cctatgactc     600
gaaggcagac atctggtccc tgggcataac agctattgaa cttgcaagag gggaaccacc    660
tcattccgag ctgcacccca tgaaagtttt attcctcatt ccaaagaaca cccaccgac    720 gttggaagga aactacagta aacccctcaa ggagtttgtg gaggcctgtt tgaataagga    780
gccgagcttt agaccactg ctaaggagtt attgaagcac aagtttatac tacgcaatgc     840
aaagaaaact tcctacttga ccgagctcat cgacaggtac aagagatgga aggccgagca    900
gagccatgac gactcgagct ccgaggattc cgacgcggaa acagatggcc aagcctcggg    960
gggcagtgat tctggggact ggatcttcac aatccgagaa aaagatccca gaatctcga   1020 gaatggagct cttcagccat cggacttgga cagaaataag atgaaagaca tcccaaagag   1080
gcctttctct cagtgtttat ctacaattat ttctcctctg tttgcagagt tgaaggagaa   1140
gagccaggcg tgcggaggga acttgggtc cattgaagag ctgcgagggg ccatctacct   1200
agcggaggag gcgtgccctg gcatctccga caccatggtg gcccagctcg tgcagcggct   1260
ccagagatac tctctaagtg gtggaggaac ttcatcccac tgaaattcct ttggcatttg   1320
gggttttgtt tttccttttt tccttcttca tcctcctcct tttttaaaag tcaacgagag   1380
ccttcgctga ctccaccgaa gaggtgcgcc actgggagcc accccagcgc caggcgcccg   1440 tccaggaca cacacagtct tcactgtgct gcagccagat gaagtctctc agatgggtgg   1500
ggagggtcag ctccttccag cgatcatttt attttatttt attactttg ttttttaattt   1560 taaccatagt gcacatattc caggaaagtg tcttaaaaa caaaaacaaa ccctgaaatg    1620
tatatttggg attatgataa ggcaactaaa gacatgaaac ctcaggtatc ctgctttaag   1680
ttgataactc cctctgggag ctggagaatc gctctggtgg atgggtgtac agatttgtat   1740
ataatgtcat ttttacggaa acctttcgg cgtgcataag gaatcactgt gtacaaactg    1800
gccaagtgct tctgtagata acgtcagtgg agtaaatatt cgacaggcca taacttgagt   1860
ctattgcctt gcctttatta catgtacatt ttgaattctg tgaccagtga tttgggtttt   1920
attttgtatt tgcagggttt gtcattaata attaatgccc ctctcttaca gaacactcct   1980
atttgtacct caacaaatgc aaattttccc cgtttgccct acgcccttt tggtacacct    2040 agaggttgat ttcctttttc atcgatggta ctatttctta gtgttttaaa ttggaacata   2100
tcttgcctca tgaagcttta aattataatt ttcagtttct ccccatgaag cgctctcgtc   2160
tgacatttgt ttggaatcgt gccactgctg gtctgcgcca gatgtaccgt cctttccaat   2220
acgattttct gttgcacctt gtagtggatt ctgcatatca tctttcccac ctaaaaatgt   2280
ctgaatgctt acacaaataa attttataac acgcttaaaa aa                      2322

<210> SEQ ID NO 2
<211> LENGTH: 1296
<212> TYPE: DNA
<213> ORGANISM: Homo Sapiens

<400> SEQUENCE: 2
```

-continued

```
atggctcact ccccggtgca gtcgggcctg cccggcatgc agaacctaaa ggcagaccca      60
gaagagcttt ttacaaaact agagaaaatt gggaagggct cctttggaga ggtgttcaaa     120
ggcattgaca tcggactca gaaagtggtt gccataaaga tcattgatct ggaagaagct     180
gaagatgaga tagaggacat tcaacaagaa atcacagtgc tgagtcagtg tgacagtcca     240
tatgtaacca atattatgg atcctatctg aaggatacaa aattatggat aataatggaa     300
tatcttggtg gaggctccgc actagatcta ttagaacctg gcccattaga tgaaacccag     360
atcgctacta tattaagaga aatactgaaa ggactcgatt atctccattc ggagaagaaa     420
atccacagag acattaaagc ggccaacgtc ctgctgtctg agcatggcga ggtgaagctg     480
gcggactttg gcgtggctgg ccagctgaca gacacccaga tcaaaaggaa caccttcgtg     540
ggcacccat tctggatggc acccgaggtc atcaaacagt cggcctatga ctcgaaggca     600
gacatctggt ccctgggcat aacagctatt gaacttgcaa gagggaacc acctcattcc     660
gagctgcacc ccatgaaagt tttattcctc attccaaaga caacccacc gacgttggaa     720
ggaaactaca gtaaaccct caaggagttt gtggaggcct gtttgaataa ggagccgagc     780
tttagaccca ctgctaagga gttattgaag cacaagttta tactacgcaa tgcaaagaaa     840
acttcctact tgaccgagct catcgacagg tacaagagat ggaaggccga gcagagccat     900
gacgactcga gctccgagga ttccgacgcg aaaacagatg ccaagcctc gggggggcagt     960
gattctgggg actggatctt cacaatccga gaaaagatc ccaagaatct cgagaatgga    1020
gctcttcagc catcggactt ggacagaaat aagatgaaag acatcccaaa gaggcctttc    1080
tctcagtgtt tatctacaat tatttctcct ctgtttgcag agttgaagga aagagccag    1140
gcgtgcggag ggaacttggg gtccattgaa gagctgcgag gggccatcta cctagcggag    1200
gaggcgtgcc ctggcatctc cgacaccatg gtggcccagc tcgtgcagcg gctccagaga    1260
tactctctaa gtggtggagg aacttcatcc cactga                             1296
```

<210> SEQ ID NO 3
<211> LENGTH: 431
<212> TYPE: PRT
<213> ORGANISM: Homo Sapiens

<400> SEQUENCE: 3

```
Met Ala His Ser Pro Val Gln Ser Gly Leu Pro Gly Met Gln Asn Leu
  1               5                  10                  15

Lys Ala Asp Pro Glu Glu Leu Phe Thr Lys Leu Glu Lys Ile Gly Lys
             20                  25                  30

Gly Ser Phe Gly Glu Val Phe Lys Gly Ile Asp Asn Arg Thr Gln Lys
         35                  40                  45

Val Val Ala Ile Lys Ile Ile Asp Leu Glu Glu Ala Glu Asp Glu Ile
     50                  55                  60

Glu Asp Ile Gln Gln Glu Ile Thr Val Leu Ser Gln Cys Asp Ser Pro
 65                  70                  75                  80

Tyr Val Thr Lys Tyr Tyr Gly Ser Tyr Leu Lys Asp Thr Lys Leu Trp
                 85                  90                  95

Ile Ile Met Glu Tyr Leu Gly Gly Gly Ser Ala Leu Asp Leu Leu Glu
            100                 105                 110

Pro Gly Pro Leu Asp Glu Thr Gln Ile Ala Thr Ile Leu Arg Glu Ile
        115                 120                 125

Leu Lys Gly Leu Asp Tyr Leu His Ser Glu Lys Lys Ile His Arg Asp
    130                 135                 140
```

-continued

```
Ile Lys Ala Ala Asn Val Leu Leu Ser Glu His Gly Glu Val Lys Leu
145                 150                 155                 160

Ala Asp Phe Gly Val Ala Gly Gln Leu Thr Asp Thr Gln Ile Lys Arg
            165                 170                 175

Asn Thr Phe Val Gly Thr Pro Phe Trp Met Ala Pro Glu Val Ile Lys
            180                 185                 190

Gln Ser Ala Tyr Asp Ser Lys Ala Asp Ile Trp Ser Leu Gly Ile Thr
        195                 200                 205

Ala Ile Glu Leu Ala Arg Gly Glu Pro Pro His Ser Glu Leu His Pro
210                 215                 220

Met Lys Val Leu Phe Leu Ile Pro Lys Asn Asn Pro Thr Leu Glu
225                 230                 235                 240

Gly Asn Tyr Ser Lys Pro Leu Lys Glu Phe Val Glu Ala Cys Leu Asn
            245                 250                 255

Lys Glu Pro Ser Phe Arg Pro Thr Ala Lys Glu Leu Leu Lys His Lys
            260                 265                 270

Phe Ile Leu Arg Asn Ala Lys Lys Thr Ser Tyr Leu Thr Glu Leu Ile
        275                 280                 285

Asp Arg Tyr Lys Arg Trp Lys Ala Glu Gln Ser His Asp Asp Ser Ser
290                 295                 300

Ser Glu Asp Ser Asp Ala Glu Thr Asp Gly Gln Ala Ser Gly Gly Ser
305                 310                 315                 320

Asp Ser Gly Asp Trp Ile Phe Thr Ile Arg Glu Lys Asp Pro Lys Asn
            325                 330                 335

Leu Glu Asn Gly Ala Leu Gln Pro Ser Asp Leu Asp Arg Asn Lys Met
            340                 345                 350

Lys Asp Ile Pro Lys Arg Pro Phe Ser Gln Cys Leu Ser Thr Ile Ile
        355                 360                 365

Ser Pro Leu Phe Ala Glu Leu Lys Glu Lys Ser Gln Ala Cys Gly Gly
370                 375                 380

Asn Leu Gly Ser Ile Glu Glu Leu Arg Gly Ala Ile Tyr Leu Ala Glu
385                 390                 395                 400

Glu Ala Cys Pro Gly Ile Ser Asp Thr Met Val Ala Gln Leu Val Gln
            405                 410                 415

Arg Leu Gln Arg Tyr Ser Leu Ser Gly Gly Thr Ser Ser His
        420                 425                 430

<210> SEQ ID NO 4
<211> LENGTH: 426
<212> TYPE: PRT
<213> ORGANISM: Homo Sapiens

<400> SEQUENCE: 4

Met Ala His Leu Arg Gly Phe Ala Asn Gln His Ser Arg Val Asp Pro
1               5                   10                  15

Glu Glu Leu Phe Thr Lys Leu Asp Arg Ile Gly Lys Gly Ser Phe Gly
            20                  25                  30

Glu Val Tyr Lys Gly Ile Asp Asn His Thr Lys Glu Val Val Ala Ile
        35                  40                  45

Lys Ile Ile Asp Leu Glu Glu Ala Glu Asp Glu Ile Glu Asp Ile Gln
50                  55                  60

Gln Glu Ile Thr Val Leu Ser Gln Cys Asp Ser Pro Tyr Ile Thr Arg
65                  70                  75                  80

Tyr Phe Gly Ser Tyr Leu Lys Ser Thr Lys Leu Trp Ile Ile Met Glu
            85                  90                  95
```

```
Tyr Leu Gly Gly Gly Ser Ala Leu Asp Leu Leu Lys Pro Gly Pro Leu
                100                 105                 110

Glu Glu Thr Tyr Ile Ala Thr Ile Leu Arg Glu Ile Leu Lys Gly Leu
            115                 120                 125

Asp Tyr Leu His Ser Glu Arg Lys Ile His Arg Asp Ile Lys Ala Ala
130                 135                 140

Asn Val Leu Leu Ser Glu Gln Gly Asp Val Lys Leu Ala Asp Phe Gly
145                 150                 155                 160

Val Ala Gly Gln Leu Thr Asp Thr Gln Ile Lys Arg Asn Thr Phe Val
                165                 170                 175

Gly Thr Pro Phe Trp Met Ala Pro Glu Val Ile Lys Gln Ser Ala Tyr
            180                 185                 190

Asp Phe Lys Ala Asp Ile Trp Ser Leu Gly Ile Thr Ala Ile Glu Leu
        195                 200                 205

Ala Lys Gly Glu Pro Pro Asn Ser Asp Leu His Pro Met Arg Val Leu
210                 215                 220

Phe Leu Ile Pro Lys Asn Ser Pro Pro Thr Leu Glu Gly Gln His Ser
225                 230                 235                 240

Lys Pro Phe Lys Glu Phe Val Glu Ala Cys Leu Asn Lys Asp Pro Arg
                245                 250                 255

Phe Arg Pro Thr Ala Lys Glu Leu Leu Lys His Lys Phe Ile Thr Arg
            260                 265                 270

Tyr Thr Lys Lys Thr Ser Phe Leu Thr Glu Leu Ile Asp Arg Tyr Lys
        275                 280                 285

Arg Trp Lys Ser Glu Gly His Gly Glu Glu Ser Ser Ser Glu Asp Ser
290                 295                 300

Asp Ile Asp Gly Glu Ala Glu Asp Gly Glu Gln Gly Pro Ile Trp Thr
305                 310                 315                 320

Phe Pro Pro Thr Ile Arg Pro Ser Pro His Ser Lys Leu His Lys Gly
                325                 330                 335

Thr Ala Leu His Ser Ser Gln Lys Pro Ala Asp Ala Val Lys Arg Gln
            340                 345                 350

Pro Arg Ser Gln Cys Leu Ser Thr Leu Val Arg Pro Val Phe Gly Glu
        355                 360                 365

Leu Lys Glu Lys His Lys Gln Ser Gly Gly Ser Val Gly Ala Leu Glu
370                 375                 380

Glu Leu Glu Asn Ala Phe Ser Leu Ala Glu Glu Ser Cys Pro Gly Ile
385                 390                 395                 400

Ser Asp Lys Leu Met Val His Leu Val Glu Arg Val Gln Arg Phe Ser
                405                 410                 415

His Asn Arg Asn His Leu Thr Ser Thr Arg
            420                 425

<210> SEQ ID NO 5
<211> LENGTH: 2322
<212> TYPE: DNA
<213> ORGANISM: Artificial Sequence
<220> FEATURE:
<223> OTHER INFORMATION: Antisense

<400> SEQUENCE: 5 tttttttaagc gtgttataaa atttatttgt gtaagcattc agacattttt aggtgggaaa      60
gatgatatgc agaatccact acaaggtgca acagaaaatc gtattggaaa ggacggtaca     120
tctggcgcag accagcagtg gcacgattcc aaacaaatgt cagacgagag cgcttcatgg     180
```

-continued

```
ggagaaactg aaaattataa tttaaagctt catgaggcaa gatatgttcc aatttaaaac      240
actaagaaat agtaccatcg atgaaaaagg aaatcaacct ctaggtgtac caaaaggggc      300
gtagggcaaa cggggaaaat ttgcatttgt tgaggtacaa ataggagtgt tctgtaagag      360 agggcatta attattaatg acaaaccctg caaatacaaa ataaaaccca aatcactggt       420
cacagaattc aaaatgtaca tgtaataaag gcaaggcaat agactcaagt tatggcctgt      480
cgaatattta ctccactgac gttatctaca gaagcacttg gccagtttgt acacagtgat      540
tccttatgca cgccgaaagg gtttccgtaa aaatgacatt atatacaaat ctgtacaccc      600
atccaccaga gcgattctcc agctcccaga gggagttatc aacttaaagc aggatacctg      660
aggtttcatg tctttagttg ccttatcata atcccaaata tacatttcag ggtttgtttt      720 tgttttttaaa gacactttcc tggaatatgt gcactatggt taaaattaaa aacaaaagta     780 ataaataaa ataaaatgat cgctggaagg agctgaccct ccccacccat ctgagagact      840
tcatctggct gcagcacagt gaagactgtg tgtgtccctg gacgggcgcc tggcgctggg      900
gtggctccca gtggcgcacc tcttcggtgg agtcagcgaa ggctctcgtt gacttttaaa      960
aaaggaggag gatgaagaag gaaaaaagga aaaacaaaac cccaaatgcc aaggaatt      1020 cagtgggatg aagttcctcc accacttaga gagtatctct ggagccgctg cacgagctgg     1080
gccaccatgg tgtcggagat gccagggcac gcctcctccg ctaggtagat ggcccctcgc     1140
agctcttcaa tggaccccaa gttccctccg cacgcctggc tcttctcctt caactctgca    1200
aacagaggag aaataattgt agataaacac tgagagaaag gcctctttgg gatgtctttc     1260
atcttatttc tgtccaagtc cgatggctga agagctccat tctcgagatt cttgggatct     1320
ttttctcgga ttgtgaagat ccagtcccca gaatcactgc ccccgaggc ttggccatct      1380 gtttccgcgt cggaatcctc ggagctcgag tcgtcatggc tctgctcggc cttccatctc     1440
ttgtacctgt cgatgagctc ggtcaagtag gaagttttct ttgcattgcg tagtataaac     1500
ttgtgcttca ataactcctt agcagtgggt ctaaagctcg gctccttatt caaacaggcc     1560
tccacaaact ccttgagggg tttactgtag tttccttcca acgtcggtgg gttgttcttt     1620
ggaatgagga ataaaacttt catggggtgc agctcggaat gaggtggttc ccctcttgca     1680
agttcaatag ctgttatgcc cagggaccag atgtctgcct tcgagtcata ggccgactgt     1740
ttgatgacct cgggtgccat ccagaatggg gtgcccacga aggtgttcct tttgatctgg     1800
gtgtctgtca gctggccagc cacgccaaag tccgccagct tcacctcgcc atgctcagac     1860
agcaggacgt tggccgcttt aatgtctctg tggattttct tctccgaatg gagataatcg     1920
agtcctttca gtatttctct taatatagta gcgatctggg tttcatctaa tgggccaggt     1980
tctaatagat ctagtgcgga gcctccacca agatattcca ttattatcca taattttgta    2040
tccttcagat aggatccata atatttggtt acatatggac tgtcacactg actcagcact    2100
gtgatttctt gttgaatgtc ctctatctca tcttcagctt cttccagatc aatgatcttt    2160
atggcaacca ctttctgagt ccgattgtca atgcctttga acacctctcc aaaggagccc    2220
ttcccaattt tctctagttt tgtaaaaagc tcttctgggt ctgcctttag gttctgcatg    2280
ccgggcaggc ccgactgcac cggggagtga gccatggcgc tc                       2322
```

<210> SEQ ID NO 6
<211> LENGTH: 46
<212> TYPE: DNA
<213> ORGANISM: Artificial Sequence
<220> FEATURE:

```
<223> OTHER INFORMATION: Primer

<400> SEQUENCE: 6
ggactcagaa agtggttgcc attcgaataa ttgatctgga agaagc        46

<210> SEQ ID NO 7
<211> LENGTH: 46
<212> TYPE: DNA
<213> ORGANISM: Artificial Sequence
<220> FEATURE:
<223> OTHER INFORMATION: Primer

<400> SEQUENCE: 7
gcttcttcca gatcaattat tcgaatggca accactttct gagtcc        46

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
gagcgccatg gctcactcc                                      19

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ggagtcagcg aaggctctcg                                     20
```

HUMAN STE20-LIKE STRESS ACTIVATED SERINE/THREONINE KINASE

Priority is claimed under 35 USC §119(a) from UK Application 9719920.2 entitled HUMAN STE20-LIKE STRESS ACTIVATED SERINE/THREONINE KINASE, filed Sep. 19, 1997; the entire disclosure of which is incorporated by reference.

FIELD OF THE INVENTION

The present invention relates to nucleic acid and amino acid sequences of a novel human Ste20-like stress-activated serine/threonine kinase and to the use of these sequences to identify compounds that modulate the signal transduction activity of the native biomolecule. The invention is also related to the diagnosis, study, prevention, and treatment of pathophysiological disorders related to the biological molecule.

BACKGROUND OF THE INVENTION

Cellular response mechanisms to stress are fundamentally important to the human immune system. Stress responses represent carefully devised cellular defense mechanisms which were developed at an early point during evolution; evidenced by the fact that biomolecules implicated in stress response exhibit remarkable similarity across the animal kingdom. Welch, W. J., et al., The Stress Response and the Immune System, Inflammation: Basic Principles and Clinical Correlates, Raven Press, Gallin, J. I.,et al., Eds., Second Edition, 41:841 (1992).

Lymphocyte activation, homing, resistance to target cell lysis, tumor antigenicity, regulation of proto-oncogene transcription, and immune surveillance are examples of immunologic functions that appear to be mediated or modulated by stress activated signal transduction molecules. Siegelman, M., et al., *Science*, 231:823 (1986); Kusher, D. I., et al., J. Immunol., 145:2925 (1990); Ullrich, S. J., et al., PNAS, 83:3121 (1986); Colotta, F., et al., Biochem. Biophys. Res. Commun., 168:1013 (1990); Haire, R. N., et al., J. Cell Biol, 106:883 (1988); Born, W., et al., Immunol. T., 11:40 (1990). The number of preactivated and MHC class II-restricted autoreactive T-lymphocytes in peripheral blood of patients with rheumatoid arhritis, for example, dramatically increases relative to the levels in healthy individuals. Similarly, peripheral blood T-lymphocytes from patients with inflammatory arthritis proliferate strongly in the absence of exogenous antigen or mitogen. Welch, W. J., et al., The Stress Response and the Immune System, Inflammation: Basic Principles and Clinical Correlates, Raven Press, Gallin, J. I., et al., Eds., Second Edition, Chapter 41, 841 (1992). Moreover, synovitis has been shown to result in the generation of oxygen-derived free radicals that act to perpetuate tissue damage. Blake, D. R., et al., Hypoxic-Reperfusion Injury in the Inflamed Human Joint, Lancet, 2:2889 (1989).

The control of hematopoiesis is a highly regulated process that responds to a number of physiological stimuli in the human body. Differentiation, proliferation, growth arrest, or apoptosis of blood cells depends on the presence of appropriate cytokines and their receptors, as well as the corresponding cellular signal transduction cascades. Hu, Mickey C.-T., et al., Genes & Development, 10:2251(1996). Generation of mature leukocytes, for instance, is a highly regulated process which responds to various environmental and physiological stimuli. Cytokines cause cell proliferation, differentiation or elimination, each of these processes being dependent on the presence of appropriate cytokine receptors and the corresponding signal transduction elements. Moreover, the stimulation of quiescent B- and T-lymphocytes occur via antigen receptors which exhibit remarkable homology to cytokine receptors. Grunicke, Hans H., *Signal Transduction Mechanisms in Cancer*, Springer-Verlag (1995). See also, Suchard, S. J., et al., Mitogen-Activated Protein Kinase Activation During IgG-Dependent Phagocytosis in Human Neutrophils, J. Immunol., 158:4961 (1997).

Distinct signaling cassettes, each containing a central cascade of kinases, respond to a variety of positive and negative extracellular stimuli, lead to changes in transcription factor activity and posttranslational protein modifications in mammalian cells. Kiefer, F., et al., EMBO, Vol. 5, 24:7013 (1996). One such protein kinase cascade, known as the mitogen-activated protein kinase (MAPK) cascade, is activated as an early event in the response of leukocytes to various stimuli. Stimulation of this pathway has been observed during growth factor-induced DNA synthesis, differentiation, secretion, and metabolism. The MAPK pathway has a critical role in the transduction of receptor-generated signals from the membrane to the cytoplasm and nucleus. Graves, J. D., et al., Protein Serine/Threonine Kinases of the MAPK Cascade, Annals New York Academy of Sciences, 766:320 (1995). It has been established that sustained activation of the MAPK cascade is not only required, but it is sufficient to trigger the proliferation of some cells and the differentiation of others. Cohen, P., Dissection of Protein Kinase Cascades That Mediate Cellular Response to Cytokines and Cellular Stress, Advances in Pharmacology, Academic Press, Hidaka, H., et al., Eds., Vol. 36, 15 (1996); Marshall, C. J., Cell, 80:179 (1995). Several interdependent biochemical pathways are activated following either stimulation of resting T-lymphocytes through the antigen receptor or stimulation of activated T-lymphocytes through the interleukin-2 (IL-2) receptor. Many of the events that occur after the engagement of either of these receptors are qualitatively similar, such as the activation of mitogen-activated protein kinase (MAPK) pathways and and preexisting transcription factors, leading to the expression of specific growth-associated genes. Symmetry of the Activation of Cyclin-dependent Kinaes in Mitogen and Growth Factor-stimulated T Lymphocytes, Jaime F. Modiano, et al., Annals New York Academy of Sciences, 766:134 (1995).

Recent evidence suggests that cellular response to stress is controlled primarily through events occurring at the plasma membrane, overlapping significantly with those important in initiating mitogenic responses. Exposure of cells to biological, chemical, or physical stress agents evokes a series of events leading to the activation of a wide group of genes including transcription factors as well as other gene products that are also rapidly and highly induced in response to mitogenic stimulation. The mitogen-activated protein kinase (MAPK) pathway has been shown to be essential for the mitogenic reponse in many systems. See, e.g., Qin, Y. et al., J.Cancer Res.Clin.Oncol., 120:519 (1994). Moreover, due to the fact that most oncogenes encode growth factors, growth factor receptors, or elements of the intracellular postreceptor signal-transmission machinery, it is becoming increasingly apparent that growth factor signal transduction pathways are subject to an elaborate network of positive and negative cross-regulatory inputs from other transformation-related pathways. Grunicke, Hans H., *Signal Transduction Mechanisms in Cancer*, Springer-Verlag (1995). The Hierarchical organization of the MAPK cascade makes integral protein kinase members particularly good targets for such "cross-talk". Protein Serine/Threonine Kinases of the MAPK Cascade, J. D. Graves, et al., Annals New York Academy of Sciences, 766:320 (1995).

Initial triggers for inflammation include physical and chemical agents, bacterial and viral infections, as well as exposure to antigens, superantigens or allergens, all of which have the potential to generate Reactive Oxygen Species (ROS) and to thereby activate second messenger signal transduction molecules. Storz, G., et al., Transcriptional Regulators of Oxidative Stress-Inducible Genes in Prokaryotes and Eukaryote, in: Stress-Inducible Cellular Responses, Feige, U., et al., Eds., Birkhauser Verlag (1996). Reactive oxygen radicals, via damage to many cellular components including DNA, can cause cell death or, if less severe, cell cycle arrest at growth-phase checkpoints. Stress damage not only activates checkpoint controls but also activates protein kinases, including the stress activated protein kinases (SAPKs), c-Raf-1 and ERKs, which are integral components of cytoplasmic signal transduction (MAPK) cascades. Pombo, C. M., et al., EMBO, Vol. 15, 17:4537 (1996); Russo, T., et al., J. Biol. Chem., 270:29386 (1995). Considering, inter alia, that stress has also been implicated in oxidant injury, atherosclerosis, neurogenerative processes, and aging, elucidation of the components of mammalian stress-induced pathways should provide more specific targets that can be exploited therapeutically. N. J. Holbrook, et al., *Stress Inducible Cellular Responses*, 273, U. Feige, et al., Eds., Birkhauser Verlag (1996).

Evidence has demonstrated that mitogen-activated protein kinase (MAPK) and stress activated protein kinase (SAPK) signal transduction pathways are responsible for triggering biological effects across a wide variety of pathophysiological conditions including conditions manifested by dysfunctional leukocytes, T-lymphocytes, acute and chronic inflammatory disease, auto-immune disorders, rheumatoid arthritis, osteoarthritis, transplant rejection, macrophage regulation, endothelial cell regulation, angiogenesis, atherosclerosis, fibroblasts regulation, pathological fibrosis, asthma, allergic response, ARDS, atheroma, osteoarthritis, heart failure, cancer, diabetes, obeisity, cachexia, Alzheimers disease, sepsis, and neurodegeneration. As MAP kinases play a central role in signaling events which mediate cellular response to stress, their inactivation is key to the attenuation of the response. N. J. Holbrook, et al., *Stress-Inducible Cellular Responses*, 273, Feige, U., et al., Eds., Birkhauser Verlag (1996).

Despite major efforts to develop new therapeutic approaches Adult Respiratory Distress Syndrome (ARDS) (acute pulmonary inflammation characterized by the massive generation of Reactive Oxygen Species (ROS) within the lung), for example, remains lethal for about 50% of affected patients. Polla. B. S., et al., Stress Proteins in Inflammation, in: *Stress Inducible Cellular Responses*, Feige, U., et al. Eds., Birkhauser Verlag (1996). Moreover, the chronic inflammatory disease, rheumatoid arthritis, for instance, is believed to be mediated by actvated T-lymphocytes that infiltrate the synovial membrane and initiate a series of inflammatory processes. Panayi, G. S., et al., The Importance of the T-Cell in Initiating and Maintaining the Chronic Synovitis of Rheumatoid Arthritis, Arthritis Rheum, 35:729 (1992). Accumulating evidence also indicates that the autoimmune disease multiple sclerosis (MS) is mediated by autoreactive T-lymphocytes. Stinissen, P., et al., Crit. Rev. Immunol., 17(1):33 (1997). Autoreactive T-lymphocytes have been demonstrated to undergo in vivo activation and clonal expansion in patients with MS. Zhang, J., et al., J. Mol. Med., 74(11):653 (1996). In diabetes mellitus, autoreactive T-lymphocytes systematically destroy pancreatic islet cells such that they prove incapable of producing insulin. Another propelling recent development in the implication of overactive T-cells is the recognition that a particular subset of T-lymphocytes appear to be a major culprit in asthma and other allergic diseases, by responding with undue vigor to apparently harmless invaders (rates of asthma per capita in the developing world have increased dramatically in the last several decades; doubling in the U.S. since 1980). New Clues to Asthma Therapies: Vogel, G., Science, 276:1643 (1997).

Recently, much progress has been made in defining the signal transduction pathways mediating the cellular response to stress. Pombo, C. M., et al., for instance, report the cloning and characterization of a human Ste20-like oxidant stress response kinase, SOK-1. The kinase is positively regulated by phohsphorylation and negatively regulated by its C-terminal non-catalytic region. Reported data suggests SOK-1 transduces signals in response to oxidative and environmental stress. EMBO, Vol. 15, 17:4537 (1996). Other stress-activated protein kinase (SAPK), members of the MAPK family, have been shown to be activated in situ by inflammatory stimuli, including tumor-necrosis factor (TNF) and interleukin-1. Kyriakis, J. M., etal., Nature, 369:156 (1994); Dérijard, B., etal., Cell, 76:025 (1994); Sánchez, I., et al., Nature, 372:794 (1994). See also, Kiefer, F., et al., EMBO, Vol. 5, 24:7013 (1996); Creasy, C. L., etal., J. Biol. Chem., 271: No. 35, 21049 (1996)); Creasy, C. L., et al., Gene, 167:303 (1995)); Manser, E., et al., Nature, 367:40 (1994); Hu, Mickey C.-T., et al., Genes & Development, 10:2251(1996); Katz, P., et al., J. Biol. Chem., (1994)); Pombo, C. M., et al., Nature, 377:750 (1995).

Integral members of cellular signaling pathways as targets for therapeutic development, for example, have been the subject to several reviews. See, e.g., Levitzki, A., Signal-Transduction Therapy: A Novel Approach to Disease Management, Eur. J. Biochem, 226:1 (1994); Powis G., The Potential for Molecular Oncology to Define New Drug Targets, in: New Molecular Targets for Cancer Chemotherapy, Workman, P., Kerr D. J., eds., CRC Press, Boca Raton Fla. (1994). As a result of the efforts of numerous laboratories, an impressive list of remarkably specific inhibitors of kinases, for instance, has become available. See, e.g., Levitzki, A., Tyrphostins: Tyrosine Kinase Blockers as Novel Antiproliferative Agents and Dissectors of Signal Transduction, FASEB; 6:3275 (1992); Workman P., et al., Discovery and Design of Inhibitors of Oncogenic Tyrosine Kinases, in: *New Approaches in Cancer Pharmacology: Drug Design and Development*, Springer, Berlin 55 (1994).

A novel class of pyridinyl imidazoles, CSAIDS [SmithKline Beecham], for instance, have been developed, that inhibit the production of the cytokines interleukin-1 (IL-1) and tumor necrosis factor (TNF-$\alpha$) in monocytes. The drug has been demonstrated to bind specifically to one protein in monocytes, termed CSBP (CSAID-binding protein), which has been isolated, cloned, and sequenced and demonstrated as a MAPK homolog. Lee, J. C., et al., Differential Effects of the Bicycliclmidazoles on Cytokine Synthesis in Human Monocytes and Endothelial Cells, Agents Actions, 41:C191 (1994); A Protein Kinase Involved in the Regulation of Inflammatory Cytokine Biosynthesis, Nature, 372:739 (1994). Moreover, as demonstrated by the identification of rapamycin as a specific inhibitor of the activation of p70 S6 kinase and the identification of compounds that inhibit the EGF receptor protein kinase very potently and that block the activation of MAP kinase kinase have demonstrated that specific inhibitors of protein kinases can indeed be developed. Alessi, D., et al., A Specific Inhibitor of the Activation of MAP Kinase Kinase-1 in vitro and in vivo, J. Biol. Chem., 279:27489 (1995); Fry, D., et al., A Specific Inhibitor of the Epidennal Growth Factor Receptor Tyrosine Kinase, Science, 265:806 (1994); Cohen, P., Dissection of Protein Kinase Cascades That Mediate Cellular Response to Cytokines and Cellular Stress, Intracellular Signal Transduction, Advances in Pharmacology, Hidaka, H., et al., Eds., Academic Press, 36:17 (1996).

Compounds which are able to modulate the activity of specific signal transduction molecules integral to specific intracellular pathways are expected to have significant potential for the ability to control or attenuate downstream physiological responses. Unfortunately, in spite of the introduction of numerous new drugs during the last three decades, there is a need for new, more efficient and less toxic compounds. Accordingly, the ability to identify such compounds is of paramount importance.

SUMMARY OF THE INVENTION

The present invention is directed to an isolated and purified polynucleotide molecule, which encodes a polypeptide of a human stress-activated signal-transduction serine/threonine kinase, or a biologically active derivative thereof comprising a nucleic acid sequence encoding the polypeptide having the sequence substantially as depicted in SEQ ID NO:3 or a biologically active fragment thereof. Isolated and purified polynucleotides of the present invention include but are not limited to SEQ ID NO:1 (novel human signal-transduction kinase cDNA) and SEQ ID NO:2 (novel human signal-transduction kinase structural coding region).

In addition, the current invention is directed to a purified polypeptide comprising the amino acid sequence substantially as depicted in SEQ ID NO:3 which functions as a human signal-transduction kinase polypeptide.

The invention is further directed to an expression vector for expression of a novel human signal-transduction kinase polypeptide in a recombinant host cell, wherein said vector contains a polynucleotide comprising a nucleic acid sequence encoding a human signal-transduction kinase polypeptide having the sequence substantially as depicted in SEQ ID NO:3 or a biologically active derivative thereof.

Further the invention is directed to a host cell containing an expression vector for expression of a novel human signal-transduction kinase polypeptide, wherein said vector contains a polynucleotide comprising a nucleic acid sequence encoding the polypeptide of a human kinase having the sequence substantially as depicted in SEQ ID NO:3 or a biologically active derivative thereof. The invention is also directed to a method for producing a polypeptide having the amino acid sequence substantially as depicted in SEQ ID NO:3 by culturing said host cell under conditions suitable for the expression of said polypeptide, and recovering said polypeptide from the host cell culture.

The instant invention is further directed to a method of identifying compounds that modulate the activity of a human signal-transduction kinase, comprising:

(a) combining a candidate compound modulator of a human signal-transduction kinase activity with a polypeptide of a human signal-transduction kinase having the sequence substantially as depicted in SEQ ID NO:3, and (b) measuring an effect of the candidate compound modulator on the kinase activity The invention is also directed to method of identifying compounds that modulate the activity of a human signal-transduction kinase, comprising:

(a) combining a candidate compound modulator of a human signal-transduction kinase activity with a host-cell expressing a polypeptide of a human signal-transduction kinase molecule having a sequence substantially as depicted in SEQ ID NO:3, and (b) measuring an effect of the candidate compound modulator on the kinase activity.

The present invention is also directed to active compounds identified by means of the aforementioned methods, wherein said compounds modulate the activity of a human signal-transduction kinase.

Further, the invention is directed to a pharmaceutical composition comprising a compound active in the aforementioned methods, wherein said compound is a modulator of a human signal-transduction kinase.

Additionally, the invention is directed to a novel treatment of a patient in need of such treatment for a condition which is mediated by a human signal-transduction kinase, comprising administration of a human signal-transduction kinase modulating compound active in the aforementioned method.

The invention is further directd to an antisense poynucleotide molecule comprising substantially the complement of SEQ ID NO:2 or a biologically-effective portion thereof, or SEQ ID NO:5 or a biologically-effective portion thereof, as well as a method for inhibiting the expression of a human signal-transduction kinase comprising administering an effective amount of the antisense molecule.

The current invention is also drawn toward an antibody specific for a purified polypeptide comprising the amino acid sequence substantially as depicted in SEQ ID NO:3, and a diagnostic composition for the identification of a polypeptide sequence comprising the amino acid sequence substantially as depicted in SEQ ID NO:3.

BRIEF DESCRIPTION OF THE FIGURES

FIG. 1 displays SEQ ID NO:1 which is a 2322 base cDNA nucleic acid sequence which encodes the novel human stress activated kinase polypeptide described herein.

FIG. 2 displays SEQ ID NO:2 which is the 1296 base translated structural region, ATG to TGA, of the cDNA nucleic acid sequence which encodes the novel human stress activated kinase polypeptide described herein.

FIG. 3 displays SEQ ID NO:3 which is the 431 amino acid residue sequence of the novel human stress activated kinase polypeptide described herein.

FIG. 4 shows SEQ ID NO:4 which is the 426 amino acid residue sequence of SOK-1, the recently described human oxidant stress activated kinase. Pombo, C. M., et al., EMBO, Vol. 15, 17:4537 (1996).

FIG. 5 shows a comparison between the amino acid residue sequence of the novel human stress activated kinase polypeptide described herein: (SEQ ID NO:3) (designated CD473313), and the amino acid residue sequences of the SOK-1 stress activated kinase (SEQ ID NO:4). Conserved amino acid residues are boxed. Dashes represent gaps introduced to optimize the alignment. Sequences shown in this figure were produced using the multisequence alignment program of DNASTAR software (DNASTAR Inc, Madison Wis.).

FIG. 7 displays SEQ ID NO:5 which is a 2322 base antisense nucleic acid sequence which is complementary to SEQ ID NO:1.

FIG. 8 displays SEQ ID NO:6 and SEQ ID NO:7 which are oligonucleotide primers used to produce a dominant negative inactive novel human stress activated kinase ($K^{53} \rightarrow R^{53}$) mutant. These primers are used to produce the mutant/pT7Blue construct (Statagene, La Jolla, Calif.).

FIG. 10 displays SEQ ID NO:8 and SEQ ID NO:9 which are oligonucleotide PCR primers used to produce full-length nucleic acid sequence pertaining to the novel human stress activated kinase.

DETAILED DESCRIPTION OF THE INVENTION

Figure 6:
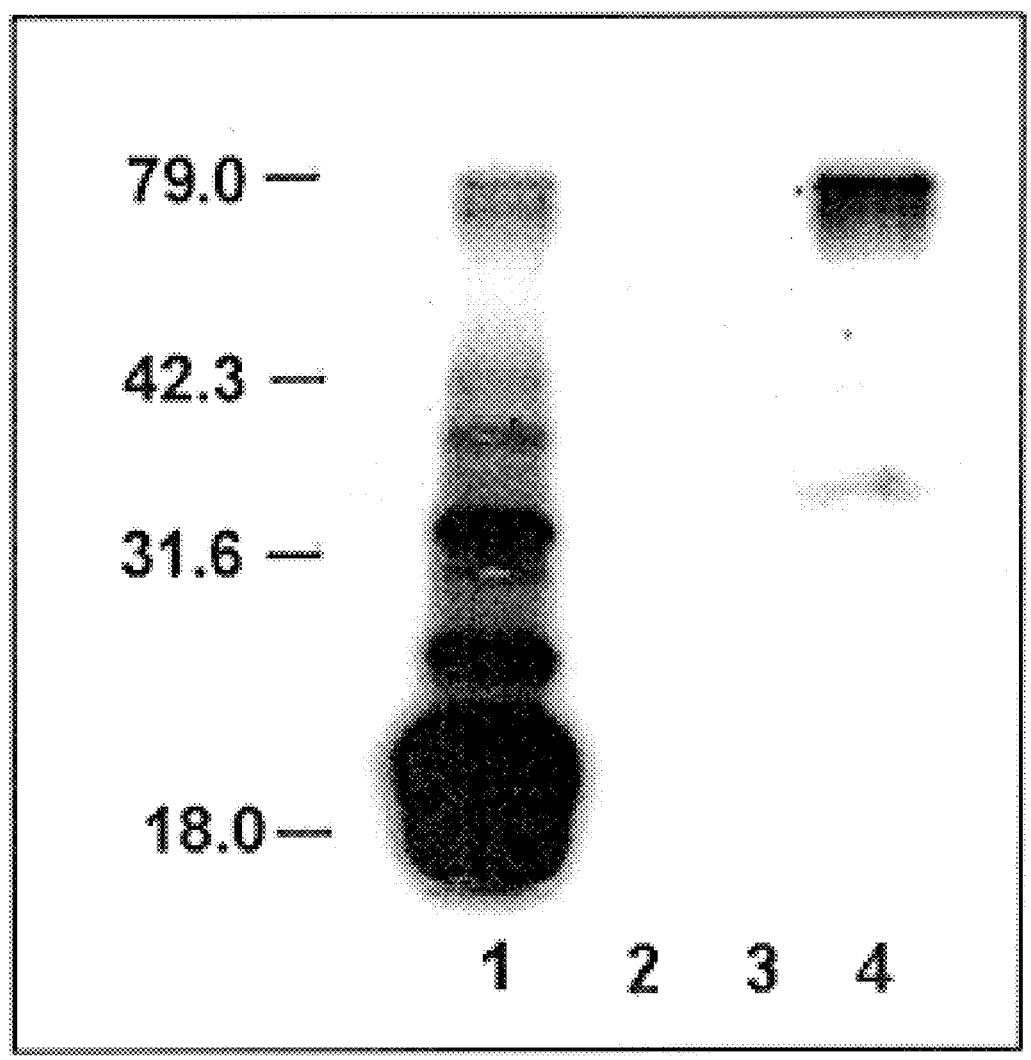
FIG. 6 displays the result of an autoradiographic assay for the kinase activity of the novel human stress activated kinase polypeptide described herein.

Unless defined otherwise, all technical and scientific terms used herein have the same meaning as is commonly understood by one of skill in the art to which this invention belongs. All publications and patents referred to herein are incorporated by reference.

Nucleic acid sequence as used herein refers to an oligonucleotide, nucleotide or polynucleotide sequence, and fragments or portions thereof, and to DNA or RNA of genomic or synthetic origin which may be double-stranded or single-stranded whether representing the sense or antisense strand. Similarly, amino acid and/or residue sequence as used herein refers to peptide or protein sequences or portions thereof.

Purified as used herein refers to molecules, either nucleic acid or amino acid sequences, that are removed from their natural environment and isolated or separated from at least one other component with which they are naturally associated.

As used herein, a functional derivative of the human signal-transduction kinase molecule disclosed herein is a compound that possesses a biological activity (either functional or structural) that is substantially similar to SEQ ID NO:3. The term "functional derivatives" is intended to include the "fragments," "variants," "degenerate variants," "analogs" and "homologues", and to "chemical derivatives". The term "variant" is meant to refer to a molecule substantially similar in structure and function to either the entire protein kinase molecule or to a fragment thereof. A molecule is "substantially similar" to the kinase polypeptide if both molecules have substantially similar structures or if both molecules possess similar biological activity. The term "analog" refers to a molecule substantially similar in function to either the entire signal transduction polypeptide, or to a fragment thereof.

"Substantially as depicted" as used herein refers to functional derivative proteins, peptides and DNA sequences that may have insignificant changes but perform substantially the same biological function in substantially the same way.

Biologically active fragment as used herein includes peptides which have been truncated with respect to the N- or C-termini, or both; or the corresponding 5' or 3' end, or both, of the corresponding polynucleotide coding region, which fragments perform substantially the same biological function or encode peptides which perform substantially the same function as the precursor. The term "biologically active" also refers to the activity of a homolog or analog entity having structural, regulatory or biochemical functions substantially the same as the naturally occurring entity.

Expression vector as used herein refers to nucleic acid vector constructions which have components to direct the expression of heterologous protein coding regions including coding regions of the present invention through accurate transcription and translation in host cells. Expression vectors usually contain a promoter to direct polymerases to transcribe the heterologous coding region, a cloning site at which to introduce the heterologous coding region, and usually polyadenylation signals. Expression vectors include but are not limited to plasmids, retroviral vectors, viral and synthetic vectors.

Transformed host cells as used herein refer to cells which have coding regions of the present invention stably integrated into their genome, or episomally present as replicating or nonreplicating entities in the form of linear nucleic acid or transcript or circular plasmid or vector.

The term "modulation" is used herein to refer to the capacity to either enhance or inhibit a functional property of the human kinase of the present invention. Such enhancement or inhibition may be contingent on the occurrence of a specific event, such as activation of a signal transduction pathway, and/or may be manifest only in particular cell types.

A cascade signal transduction mechanism is essentially a conduit for the transmittal of an external stimulus to the cell nucleus in order to trigger a distinct pattern of gene expression in response to the stimulation. The extracellular signal is amplified and transduced by a series of independent sequential covalent modifications, from the plasma membrane to the nucleus, via distinct phosphorylation steps of independently specific cognate cytosolic biomolecules. Protein phosphorylation is now acknowledged as the most important means of acute regulation of protein function, signal transduction, and gene expression in eukaryotic cells. Intracellular biomolecule phosphorylation via specific kinases is responsible for switching of cellular activity from one state to another. It is the major mechanism by which cells respond to extracellular signals such as mitogenic stimulation; biological, chemical, and physical stress, hormones, and growth factors. Protein Phosphorylation, Hardie, D. G., Oxford Press (1993).

The protein kinases are a large family of enzymes. Conserved structural motifs provide clear indications as to how the kinases transfer the γ-phosphate of a purine nucleotide triphosphate to the hydroxyl groups of their protein substrates. There are two main subdivisions within the superfamily: the protein-serine/threonine kinases and the protein-tyrosine kinases. The kinase domains that define protein kinases contain 12 conserved subdomains (I–XII) that fold into a common catalytic core structure, as revealed by the 3-dimensional structures of several enzymes. The central core of the catalytic domain, the region with greatest frequency of highly conserved residues, consists of subdomains VI through IX. The most striking indicator of amino acid specificity is found in subdomain VI, the consensus in this region is a strong indicator of serine/threonine specificity. See, e.g., Hanks, S. K., et al., The Protein Kinase Family: Conserved Features and Deduced Phylogeny of the Catalytic Domains, Science, 241:42 (1988); Hanks, S. K., et al., The Eukaryotic Protein Kinase Superfamily: Kinase (Catalytic) Domain Structure and Classification, FASEB, Ser. Rev., 9:576 (1995).

Protein kinases which have closely related catalytic domains, and thus define a family, represent products of genes that have undergone relatively recent evolutionary divergence. Clustering appears to be of predictive value in the determination of the properties and function of novel protein kinases.

Accordingly, members of a given family tend also to share related functions. This is manifest by similarities in overall structural topology, mode of regulation, and substrate specificity. See, generally, Hardie, D. G,. et al., The Protein Kinase Factsbook, Academic Press, London (1995).

Progress has been made by many labs in defining signaling pathways initiated by mitogenic stimuli. Blenis, J., Signal Transduction via the MAP Kinases, PNAS, 90:5889 (1993). The MAP kinase family of enzymes have been implicated as common and essential components of signaling pathways induced by diverse mitogenic stimuli. Once activated, MAP kinases phosphorylate a number of substrates including transcription factors essential for triggering gene expression required for the growth response. Accordingly, the MAP kinases are considered to be potentially valuable pharmacological targets within the growth factor signaling pathways. Hidaka, H., et al., Intracellular Signal Transduction, Advances in Pharmacology, Academic Press (1996).

Mitogen-activated protein kinases (MAPKs) and their upstream regulatory kinases comprise functional units that couple upstream input signals to a variety of outputs. MAPK cascades have been remarkably conserved in evolution. The core of these cascades is a three-tiered module consisting of an MAPK-extracellular signal-regulated kinase kinase (an MEKK), an MEK and an MAPK or extracellular signal-regulated kinase (ERK). The defining characteristic of these modules is the MAPK itself. The classical pathway, known as the extracellular signal-regulated kinase pathway (ERK), is activated by mitogens and growth factors. ERK has a regulatory kinase, MAPK kinase or MEK, necessary for activation. This enzyme is in turn regulated by another MAPKK kinase known as Raf. Analogous with the classical MAPK module are two other modules which are activated by cytokines and cellular stresses and which have become known as the stress kinase pathways. The defining MAPKs of these pathways are JNK (SAPK) and P38. JNK is activated by the upstream SEK-1 (MKK4) which is activated by MEKK1 or MLK3 whereas P38 is activated by MKK3 and MKK6.

In yeast the MAPK modules operate in a linear manner linking extracellular signals to functional response, whereas in mammalian cells 'cross-talk' between modules may be obligatory in some cases (eg. IL-2 production by T-lymph6cytes). Phosphorylation of transcriptional factors (eg. AP-1, NF-kB, ELK-1, ATF-2) by the terminal MAPKs serve to regulate expression of key inflammatory genes. Differences in the expression of the various kinases between cell types cell types and within in response to processes in disease will have major impact on how cells respond to extracellular stimuli under physiological and pathological conditions. It is for these reasons that there is very likely to be selectivity for specific inhibitors of these different kinases for their associated physiological role as well as opportunities for therapeutic intervention.

Phosphorylation of transcriptional factors (eg. AP-1, NF-kB, ELK-1, ATF-2) by the terminal MAPKs serve to regulate expression of key inflammatory genes. Differences in the expression of the various kinases between cell types in response to processes in disease will have major impact on how cells respond to extracellular stimuli under physiological and pathological conditions. This should provide opportunities for therapeutic intervention.

Studies of the budding and fission yeasts, *Saccharomyces cerevisiae* and *Schizosaccharomyces pombe*, have been particularly fruitful in the recognition of protein kinases. Hanks, S. K., et al., The Eukaryotic Protein Kinase Superfamily, FASEB Ser. Rev., 9:576 (1995). Signal transduction pathways connecting cell surface receptors with each member of the MAPK superfamily in mammalian cells are remarkably similar to those of the budding yeast *Saccharamyces cerevisiae*, in which genetic studies have shown parallel signaling cascades leading to the activation of at least three distinct MAPK-related kinases. Hu, Mickey C.-T., et al., Genes & Development, 10:2251(1996); See, e.g., Herskowitcz, I., etal., Cell, 80:187 (1995).

A component of the pheromone-response pathway in budding yeast, Ste20, represented the first identified member of a new family of serine/threonine protein kinases. Leberer, E., et al., EMBO, 11:4815 (1992); Ramer, S. W., et al., PNAS, 90:452 (1993). Several mammalian homologs to Ste20 have since been identified, including MST1 (Creasy, C. L., et al., J. Biol. Chem., 271: No. 35, 21049 (1996)), MST2 (Gene, 167:303 (1995)), HPK1 (Kiefer, F., et al., EMBO, Vol. 5, 24:7013 (1996)). Recently, mammalian Ste20-like kinases, including p21-activated protein kinase (PAK1) (Manser, E., et al., Nature, 367:40 (1994)) and germinal center kinase (GC kinase) (Katz, P., et al., J. Biol. Chem., (1994)), have been shown to be capable of activating mammalian MAPK cascades. Pombo, C. M., et al., EMBO, Vol. 15, 17:4537 (1996). See also, U.S. Pat. No. 5,605,825, Human PAK65, issued Feb. 25, 1997. Methods described in U.S. Pat. No. 5,605,825 are herein incorporated herein by reference.

The MAP kinases require activation by a MAPK/ERK activating kinase (MEK). The dual-specificity kinase is capable of phosphorylating both tyrosine and serine/threonine residues in proteins. The proto-oncogene c-Raf-1, for instance, has been shown to encode a protein acting as a MEK kinase and the pathway Raf→MEK→MAPK is now well established as a major signal transduction pathway for growth factors. Activated MAPK undergoes a translocation to the nucleus where it can directly phosphorylate and activate a variety of transcription factors including c-Myc, C/EBPβ, p62$^{TCF}$/Elk-1, ATF02 and c-Jun. Grunicke, Hans H., *Signal Transduction Mechanisms in Cancer*, Springer-Verlag (1995).

The MAP kinase (MAPK) cascade is critical in mediating several intracellular actions. In one pathway a series of protein-protein interactions is triggered at the plasma membrane that culminate in activation of the GTP-binding protein Ras. GTP-Ras then interacts with the protein kinase Raf, recruiting it to the plasma membrane where it is activated. The activation of Raf is followed by the sequential activation of three additional kinases: MAP kinase kinase (MAPKK), MAPK, and MAPK-activated protein (MAPKAP) kinase-1. The activation of MAPK and MAPKAP kinase-1 leads to their translocation from the cytosol to the nucleus where they regulate the activities of transcription factors. Cohen, P., Dissection of Protein Kinase Cascades That Mediate Cellular Response to Cytokines and Cellular Stress, Advances in Pharmacology, Academic Press, Hidaka, H., et al., Eds., Vol. 36, 15 (1996); Marshall, C. J., Cell, 80:179 (1995).

Recent evidence suggests that cellular response to stress is controlled primarily through events occurring at the plasma membrane, overlapping significantly with those important in initiating mitogenic responses. Exposure of cells to stress agents, as mentioned supra, evokes a series of events leading to the activation of a wide group of genes including transcription factors as well as other gene products that are also rapidly and highly induced in response to mitogenic stimulation. Pathways which are involved in mediating these cellular responses rely on the activation of mitogen-activated protein kinases (MAPK) which include extracellular signal-regulated kinases (ERK), stress activated protein kinases (SAPK), c-Jun N-terminal kinases (JNK), and p38/PK/CSBP kinases. These kinases play a key role in the activation of transcription factors and other regulatory proteins involved in activating gene expression. Phosphorylation enhances complex formation and the serum response element located in the promoters of stress response genes such as c-fos. Other regulated proteins include p90$^{RSK}$, activating transcription factor-2 (ATF-2, a cAMP response element-binding protein), NF-IL6 (nuclear factor for the activation of Interleukin 6) and c-Myc. Davis, R. J., The Mitogen-Activated Protein Kinase Signal Transduction Pathway, J. Biol. Chem., 268:1553 (1993); N. J. Holbrook, et al., Stress Inducible Cellular Responses, 273, in: Stress-Inducible Cellular Responses, Feige, U., et al., Eds., Birkhauser Verlag (1996). The mitogen-activated protein kinase (MAPK) pathway has been shown to be essential for the mitogenic reponse in many systems. See, e.g., Qin, Y. et al., J.Cancer Res.Clin.Oncol., 120:519 (1994). Moreover, due to the fact that most oncogenes encode growth factors, growth factor receptors, or elements of the intracellular postreceptor signal-transmission machinery, it is becoming increasingly apparent that growth factor signal transduction pathways are subject to an elaborate network of positive and negative cross-regulatory inputs from other transformation-related pathways. Grunicke, Hans H., *Signal Transduction Mechanisms in Cancer*, Springer-Verlag (1995). The Hierarchical organization of the MAPK cascade makes integral protein kinase members particularly good targets for such "cross-talk". Protein Serine/Threonine Kinases of the MAPK Cascade, J. D. Graves, et al., Annals New York Academy of Sciences, 766:320 (1995).

Initial triggers for inflammation include physical and chemical agents, bacterial and viral infections, as well as exposure to antigens, superantigens or allergens, all of which have the potential to generate Reactive Oxygen Species (ROS) and to thereby activate second messenger signal transduction molecules. Reactive oxygen species are generated from molecular oxygen and include the free radicals superoxide ($.O_2^-$), hydroxyl (.OH) and nitric oxide (NO.), as well as non-radical intermediates such as hydrogen peroxide ($H_2O_2$) and singlet oxygen ($^1O_2$). During normal cellular respiration, ROS are constantly produced at low rate in both eukaryotes and prokaryotes. At these low concentrations, ROS can act as second messengers, stimulate cell proliferation, and act as mediators for cell activation. However, during phagocytosis, infection or inflammation, ROS can accumulate to toxic levels which leads to oxidative stress, and may damage almost all cellular components. All organisms have mechanisms to detoxify the oxidants or to repair the damage caused by ROS, including superoxide dismutases, catalases, peroxidases, glutathione, thioredoxin, and heat shock proteins. The expression of the genes coding these proteins (oxidative stress genes) is induced by changes in the concentrations of ROS, suggesting that cells have developed mechanisms to sense the ROS. Storz, G., et al., Transcriptional Regulators of Oxidative Stress-Inducible Genes in Prokaryotes and Eukaryote, in: Stress-Inducible Cellular Responses, Feige, U., et al., Eds., Birkhauser Verlag (1996).

Isozymes Generally

The study of isozymes has grown into one of fundamental significance in the investigation of the molecular basis of cellular differentiation and morphogenesis. Isozymes represent a metabolic type of regulation accomplished through the participation of multiple forms of a given enzyme or enzyme subunits that occur within an organism, in different cell types, or even within a single cell. In many instances all forms of the particular enzyme catalyze the same overall reaction but differ in their dependence on substrate concentration, ionic cofactors, and cellular conditions. Isozymes such as lactate dehydrogenase, for example, occur in five different forms of approximately the same molecular weight. Although predominantly in skeletal muscle, lactate dehydrogenase isozymes exist in different proportions in different tissues such as cardiac and red muscle tissue, as well as embryonic tissues. The relative proportions of the lactate dehydrogenase, for example, set of isozymes in particular tissues is particularly important in the diagnosis of heart and liver disease. The A4 and A3B isozymes are elevated in liver disease, therefore the blood serum factor isozyme levels of lactate dehydrogenase, for instance, are used in clinical diagnoses. Isozymes are now known for a great many different enzymes. Many allosteric enzymes occur as two or more isozymes that vary in sensitivity to their allosteric modulators. Different isozymes have accordingly evolved as mechanistic response to biochemical stress—their presence therefore is a reliable factor in the indication of precise physiological conditions.

SOK-1

Pombo et al. recently reported the cloning and characterization of human Ste20/oxidant stress response kinase, SOK-1 which belongs to the Sps1/GC kinase group of Ste20-like kinases with N-terminal catalytic domains. The kinase is positively regulated by phohsphorylation and negatively regulated by its C-terminal non-catalytic region. SOK-1 is activated relatively specifically by oxidant stress. Reported data places SOK-1 in a stress response pathway and suggest it resembles in function yeast Ste20s which transduce signals in response to environmental stress. EMBO, Vol. 15, 17:4537 (1996). The open reading frame is reported to encode a protein of 426 amino acids and has a predicted $M_r$ of 48,041 Da. The kinase domain is located in the N-terminal half of the protein. The reported peptide contains all 11 subdomains of serine/threonine kinases. Ste20 related stress-activated kinases are evidenced to be in proximity to the membrane in the signaling cascade and therefore are able to provide greater target opportunity for selective modulation of signal transduction. See, Schinkman, K., et al., Cloning and Characterization of a Human STE20-Like Protein Kinase with Unusual Cofactor Requirements, J. Biol. Chem., 272 (45): 28695–28703 (Nov. 7, 1997); GENBANK locus AF024636 1970 bp mRNA PRI 02-NOV-1997, Definition: Homo sapiens STE20-like kinase 3 (mst-3) mRNA, NID g2582412.

Novel Signal-transduction Kinase

A novel human stress-activated signal transduction serine/threonine protein kinase molecule, as well as example nucleic acid sequences which encode therefor, are herein described.

A cDNA sequence is provided, (SEQ ID NO:1) FIG. 1, which comprises the structural coding region of the native human signal transduction kinase (SEQ ID NO:2) FIG. 2. The 2322 bp SEQ ID NO:1 contiguous cDNA sequence contains a 1293 bp open reading frame (ORF) with a Kozak initiation sequence at the start methionine. The SEQ ID NO:1 region which encodes the structural biomolecule, (SEQ ID NO:3) FIG. 3, extends from the ATG translation initiation codon beginning at base position 8 to the CAC final open reading frame codon ending at base position 1300

(bases 1301–1303 represent the Opal native termination codon TGA). FIG. 2 (SEQ ID NO:2), shows the 1296 base open reading frame including the stop codon. The native human homolog of the Ste20-like stress-activated kinase (SEQ ID NO:3) is shown in FIG. 3. The 431 amino acid residue sequence of the novel protein contains all eleven (11) sudomains found in eukaryotic protein kinases including Ste20-like kinases. The protein has a predicted $M_r$ of 47,919 Da, an isolectric point of 5.24, and a net charge of −12.68.

Figure 5:
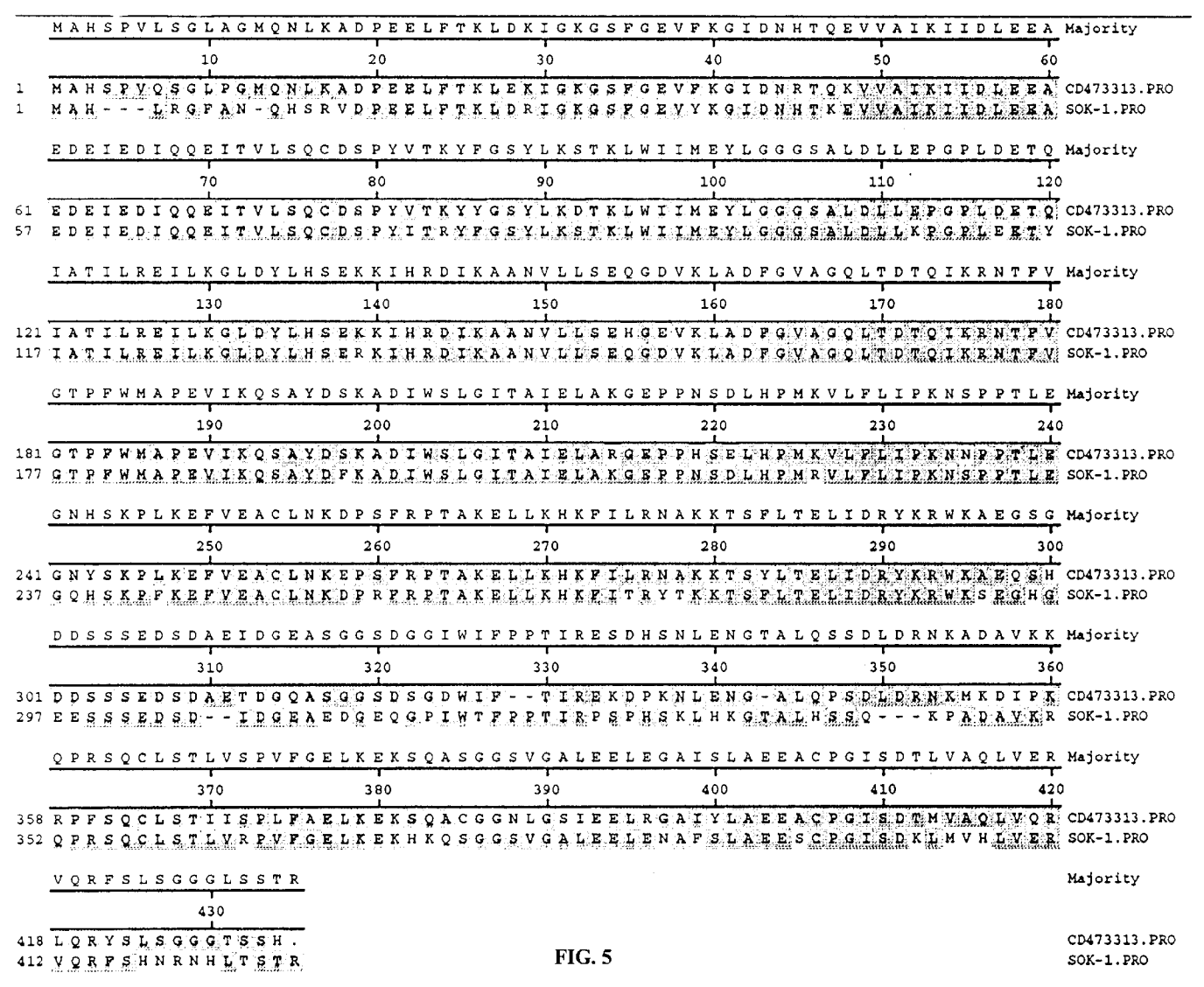

Mitogen-activated protein kinase cascades have been remarkably conserved in evolution. FIG. 4, for example, shows the 426 amino acid residue sequence of SOK-1 (SEQ ID NO:4) which is the recently described human MAPK-pathway oxidant (stress) activated kinase. SOK-1 has been characterized as a human homolog of the MAPK-pathway yeast stress-activated kinase Ste20. Pombo, C. M., et al., EMBO, Vol. 15, 17:4537 (1996). FIG. 5 shows a comparison between the amino acid residue sequence of the human stress activated kinase described herein.(SEQ ID NO:3) (designated CD473313), and the amino acid residue sequences of the SOK-1 stress activated kinase (SEQ ID NO:4). Conserved amino acid residues are boxed. Dashes represent gaps introduced to optimize the alignment. Sequences shown in this figure were produced using the multisequence alignment program of DNASTAR software (DNASTAR Inc, Madison Wis.). The novel human stress-activated signal transduction serine/threonine protein kinase molecule (SEQ ID NO:3) has 70% amino acid residue homology to the previously reported human Ste20-like homolog SOK-1 (SEQ ID NO:4). Pombo et al. reported SEQ ID NO:4 as a human Ste20/oxidant stress response kinase. Ste20 related stress-activated kinases, via evidentiary characterization, appear to be close to the plasma membrane in the signaling cascade and therefore may have significant potential to provide greater target opportunity for selective modulation of signal transduction. Pombo, C. M., et al., EMBO, Vol. 15, 17:4537 (1996).

An example chimeric fusion peptide, comprised of Glutathionine S-transferase (GST) and the novel human kinase desciber herein, is demonstrated to phosphorylate myelin basic protein (MBP) as well as to autophosphorylate in vitro—described in EXAMPLE I, as well as the autoradiograph shown in FIG. 6. The catalytic domain of the novel stress-activated kinase (SEQ ID NO:3 residues 24–295) demonstrates 88.6 percent homologous identity with the catalytic domain of SOK-1 (SEQ ID NO:4 residues 20–291). The catalytic domain can be further divided into 12 subdomains defined by strings of conserved residues. The sequence GKGSFGEV, for instance, amino acid residue positions 31–38 of SEQ ID NO:3, corresponds to the general consensus GxGxxGxV found in subdomain I of protein kinases. The subdomain II of protein kinases, identified by a conserved lysine (K) in the tripeptide sequence AxK, is generally accepted to be involved in the phosphotransfer reaction. The novel kinase described herein demonstrates this consensus sequence in SEQ ID NO:3 residues 51–53 (AIK). Other functionally important subdomains of the protein kinase family are subdomains VI through IX. These particular regions are generally accepted to form the central core of the catalytic site—characterized by series of highly conserved residues. These domains include the generally conserved residues Asp(D)$^{166}$ and Asn(N)$^{171}$ in subdomain VI and Asp(D)$^{184}$, Phe(F)$^{185}$, and Gly(G)$^{186}$ in subdomain VII; all of which have been implicated in ATP binding (reference amino acid residue positions are based on positions in the catalytic subunit of α form cAMP-dependent protein kinase). Region VIB contains the consensus sequence HRDLxxxN, with D being the heretofore invariant Asp(D)$^{166}$. The novel human kinase, SEQ ID NO:3 residues 142–149 in this region show HRDIKAAN wherein a conservative substitution of Ile(I) for Leu(L) is apparent. Furthermore, the stress-activated signal transduction kinase molecule described herein, SEQ ID NO:3, contains the conserved DFG residues 162–164 of subdomain VII. The Asp(D) is generally accepted to functionally orient the γ-phosphate of the ATP for transfer in phosphorylation. Subdomain VIII of the novel kinase contains the highly conserved APE sequence, with the Glu(E) SEQ ID NO:3 residue 189, corresponding to the invariant Glu(E)$^{208}$. This particular subdomain is thought to play a critical role in the recognition of substrate binding. Additionally, many kinases are activated by phosphorylation of residues in subdomain VIII. The consensus sequence DxWS/AxG of subdomain IX is represented by amino acid residues 201–206 of SEQ ID NO:3 (DIWSLG). This region is believed to form a large α-helix while the initial Asp(D) of the consensus sequence serves to stabilize the catalytic loop by hydrogen bonding.

Variations

The present invention also encompasses variants of the human signal-transduction kinase molecule SEQ ID NO:3. A preferred variant substantially as depicted in SEQ ID NO:3, for instance, is one having at least 80% amino acid sequence similarity; a more preferred variant is one having at least 90% amino acid sequence similarity; and a most preferred variant is one having at least 95% amino acid sequence similarity to the kinase molecule amino acid sequence (SEQ ID NO:3) or a biologically active fragment thereof.

A "variant" of the human kinase molecule of the present invention may have an amino acid sequence that is different by one or more amine acid "substitutions". The variant may have "conservative" changes, wherein a substituted amine acid has similar structural or chemical properties, eg, replacement of leucine with isoleucine. More rarely, a variant may have "nonconservative" changes, eg, replacement of a glycine with a tryptophan. Similar minor variations may also include amine acid deletions or insertions, or both. Guidance in determining which and how many amine acid residues may be substituted, inserted or deleted without abolishing biological or immunological activity may be found using computer programs well known in the art, for example, DNAStar software.

The present invention relates to nucleic acid (SEQ ID NO:1 and SEQ ID NO:2) and amino acid sequences (SEQ ID NO:3) of the novel human kinase and variations thereof and to the use of these sequences to identify compounds that modulate the activity of the kinase, as described infra.

The invention further relates to the use of the human signal-transduction kinase molecule in expression systems as assays for agonists or antagonists of the biomolecule. The invention also relates to the diagnosis, study, prevention, and treatment of disease related to the biological signals transduced by the serine/threonine kinase described herein.

Polynucleotide sequences which encode the human human signal-transduction kinase SEQ ID NO:3 or a functionally equivalent derivative thereof may be used in accordance with the present invention which comprise deletions, insertions and/or substitutions of the SEQ ID NO:2 nucleic acid sequence. Biologically active variants of the kinase molecule of the present invention may also be comprised of deletions, insertions or substitutions of SEQ ID NO:3 amino acid residues. A purified polynucleotide comprising a nucleic acid sequence encoding the polypeptide having the sequence substantially as depicted in SEQ ID NO:3 or a biologically active fragment thereof is a particularly preferred embodiment of the present invention.

Amino acid substitutions of SEQ ID NO:3 may be made, for instance, on the basis of similarity in polarity, charge, solubility, hydrophobicity, hydrophilicity, and/or the amphipathic nature of the residues as long as the biological activity of the kinase is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Nucleic acid sequences which encode the amino acid sequence of the kinase molecule described herein are of an exponential sum due to the potential substitution of degenerate codons (different codons which encode the same amino acid). The oligonucleotide sequence selected for heterologous expression is therefore preferably tailored to meet the most common characteristic tRNA codon recognition of the particular host expression system used as well known by those skilled in the art.

Suitable conservative substitutions of amino acids are known to those of skill in this art and may be made without altering the biological activity of the resulting polypeptide, regardless of the chosen method of synthesis. The phrase "conservative substitution" includes the use of a chemically derivatized residue in place of a non-derivatized residue provided that such polypeptide displays the desired binding activity. D-isomers as well as other known derivatives may also be substituted for the naturally occurring amino acids. See, e.g., U.S. Pat. No. 5,652,369, Amino Acid Derivatives, issued Jul. 29, 1997. Substitutions are preferably, although not exclusively, made in accordance with those set forth in TABLE I as follows:

TABLE 1

| Original residue | Example conservative substitution |
|---|---|
| Ala (A) | Gly; Ser; Val; Leu; Ile; Pro |
| Arg (R) | Lys; His; Gln; Asn |
| Asn (N) | Gln; His; Lys; Arg |
| Asp (D) | Glu |
| Cys (C) | Ser |
| Gln (Q) | Asn |
| Glu (E) | Asp |
| Gly (G) | Ala; Pro |
| His (H) | Asn; Gln; Arg; Lys |
| Ile (I) | Leu; Val; Met; Ala; Phe |
| Leu (L) | Ile; Val; Met; Ala; Phe |
| Lys (K) | Arg; Gln; His; Asn |
| Met (M) | Leu; Tyr; Ile; Phe |
| Phe (F) | Met; Leu; Tyr; Val; Ile; Ala |
| Pro (P) | Ala; Gly |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala |

The nucleotide sequences of the present invention may also be engineered in order to alter a coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, etc.

Included within the scope of the present invention are alleles of the human signal-transduction kinase molecule of the present invention. As used herein, an "allele" or "allelic sequence" is an alternative form of the kinase molecule described herein. Alleles result from nucleic acid mutations and mRNA splice-variants which produce polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

The present invention relates, in part, to the inclusion of the polynucleotide encoding the novel human signal-transduction kinase molecule in an expression vector which can be used to transform host cells or organisms. Such transgenic hosts are useful for the production of the protein kinase.

The nucleic acid sequence also provides for the design of antisense molecules useful in downregulating, diminishing, or eliminating expression of the genomic nucleotide sequence in cells including leukocytes, endothelial cells, and tumor or cancer cells.

The human signal-transduction kinase molecule of the present invention can also be used in screening assays to identify antagonists or inhibitors which bind, emulate substrate, or otherwise inactivate or compete with the biomolecule. The novel kinase can also be used in screening assays to identify agonists which induce the production of or prolong the lifespan of the molecule in vivo or in vitro.

The invention also relates to pharmaceutical compounds and compositions comprising the kinase molecule substantially as depicted in SEQ ID NO:3, or fragments thereof, antisense molecules capable of disrupting expression of the naturally occurring gene, and agonists, antibodies, antagonists or inhibitors of the native signal-transduction kinase. These compositions are useful for the prevention or treatment of conditions associated with abnormal expression of the signal transduction molecule such as described infra.

Pharmacological Significance

Compounds which are able to modulate the activity of specific signal transduction molecules integral to specific intracellular pathways are expected to have significant potential for the ability to control or attenuate downstream physiological responses. Significant evidence has been provided that stress kinase activation pathways are responsible for biological effects across a wide variety of disease areas. As MAP kinases play a central role in signaling events which mediate cellular response to stress; compounds which modulate or inactivate specific integral signal transduction molecules, i.e., the novel human stress-activated serine/threonine signal transduction kinase molecule described herein, SEQ ID NO:3, and nucleic acid sequences coding therefor, e.g. SEQ ID NO:1 and SEQ ID NO:2, have significant potential for the ablity attenuate pathophysiological responses. Accordingly, the ability to screen for antagonists and agonists which modulate the activity of the native human stress-activated serine/threonine signal transduction kinase molecule described herein is significantly valuable toward the identification and development of therapeutic agents.

Potential diagnostic and therapeutic applications are readily apparent for modulators of the human Ste20-like stress-activated serine/threonine kinase described herein.

Areas which are common to disease particularly in need of therapeutic intervention include but are not limited to pathophysiological disorders manifested by dysfunctional leukocytes, T-cell activation, acute and chronic inflammatory disease, auto-immune disorders, rheumatoid arthritis, osteoarthritis, transplant rejection, macrophage regulation, endothelial cell regulation, angiogenesis, atherosclerosis, vascular disease, fibroblasts regulation, pathological fibrosis, asthma, allergic response, ARDS, atheroma, osteoarthritis, heart failure, cancer, diabetes, obeisity, cachexia, Alzheimers, sepsis, neurodegeneration, and related disorders.

Oxidants, mechanical stress, UV irradiation, and immunologic mediators lead to the activation of proinflammatory gene products, apoptosis-related genes, and acute phase response genes. These responses are the underlying causes of vascular injury and inflammation. In view of the recent literature, it is generally accepted that MAPK pathways including the SAPK/JNK and p38 kinase pathways, for example, are central components in the response of cells to chemical, mechanical and proinflammatory assaults. With such a prominent role in cell activation, stress kinases are likely to play an important role in disease areas including, but not limited to, stroke (ischemia reperfusion), ARDS, sepsis, neurodegeneration, and inflammation. During reperfusion of ischemic tissue, for instance, there is a marked increase in stress activated protein kinase activity leading to c-Jun/ATF-2 activation to enhance gene transcription leading to either apoptosis or differentiation and cell repair. In the inflammatory response, TNF-α and IL-1β activate p38, which triggers production of more TNF and IL-1, which amplifies the inflammatory response. This process is thought to play a role in both septic shock and formation of the athersclerotic plaque. SAPKs are also thought to play a role in the induction of E-selectin expression in endothelial cells and matrix metalloproteinases in inflammatory cells, indicating a role for SAPKs in postischemic injury and tissue remodeling. Moreover, SAPK-p46β$_1$, a brain-specific kinase, colocalizes with the prominent Alzheimer's disease marker, ALZ-50, suggesting that the proline-directed hyperphosphorylation of tau protein is catalyzed by this kinase.

The signal-transduction kinase homolog described herein (SEQ ID NO:3) is believed to transduce cellular response to stressors leading to the activation of proinflammatory gene products. The deleterious effects of the mediators of inflammation, including ROS and cytokines, open new avenues for the development of original anti-inflammatory therapies. As MAP kinases play a central role in signaling events which mediate cellular response to stress, their inactivation or antagonization is key to the attenuation of the response. Clear evidence has been shown, for instance, that ERK and JNK pathways are strongly linked to IL-2 production. ERK and JNK pathways are clearly established to be required for full T-lymphocyte activation leading to IL-2 gene transcription and T-cell proliferation. Interruption of the signaling process by selective kinase inhibition is therefore expected to reduce IL-2 production and T-lymphocyte proliferation which would be therapeutically beneficial in chronic inflammatory diseases. MAPKs including stress activated kinases are expected to play key roles in the pathology of autoimmune diseases including but not limited to rheumatoid arthritis (RA), osteoarthritis (OA), and multiple sclerosis (MS). Accordingly, the novel human serine/threonine stress-activated kinase signal transduction molecule described herein (SEQ ID NO:3), and nucleic acid sequences coding therefor, e.g. SEQ ID NO:1 and SEQ ID NO:2, have significant potential as a specific targets that can be exploited diagnostically and therapeutically for the control of dysfunctional leukocytes, including but not limited to dysfunctional T-lymphocytes, and in the treatment of autoimmune disease including rheumatoid arthritis (RA) and osteoarthritis (OA), and in the study, diagnosis, and treatment of acute and chronic inflammation including but not limited to conditions such as asthma and ARDS as well as other diseases manifested by dysfunctional leukocytes.

Excess production of oxidants is responsible for the activation of MAPK pathways. Excess production of oxidants is also common to the major atherosclerotic risk factors as well as to ischaemic reperfusion injury. Lipid peroxidation in cell membranes, cytoplasmic free radicals, together with 'oxidative stress' lead to activation of AP-1 and NF-kB. The JNK pathway has been established as well as activation of Ras appears to be involved in the responses. Stimulation of macrophages and endothelial cells by LPS or TNF/IL-1 results in the activation of MAPK, JNK and P38 pathways. The selective P38 inhibitor SB203580, for example, has been clearly shown to inhibit production of TNF and IL-1 by LPS-stimulated macrophages as well as TNF, IL-6 and IL-8 by TNF-stimulated HUVECs. Philip Cohen, Dissection of Protein Kinase Cascades That Mediate Cellular Response to Cytokines and Cellular Stress, in: Intracellualr Signal Transduction, Advances in Pharmacology, Vol. 36, Academic Press (1996). MAPK pathways are also activated by shear stress. Atherosclerotic lesions develop and progress in areas of low and unstable shear stress and not in areas exposed to steady shear. Acute changes in shear stress activate MAPK pathways and chronic stress desensitizes MAPK and NF-kB pathways indicating that these pathways are activated. Transient shear stress can activate inflammatory genes partly through activation of the JNK pathway and AP-1 although the ERK pathway is also activated. Despite major efforts to develop new therapeutic approaches Adult Respiratory Distress Syndrome (ARDS) (acute pulmonary inflammation characterized by the massive generation of Reactive Oxygen Species (ROS) within the lung) remains lethal for about 50% of affected patients. Polla. B. S., et al., Stress Proteins in Inflammation, in: *Stress Inducible Cellular Responses*, Feige, U., et al. Eds., Birkhauser Verlag (1996). Accordingly, the novel human serine/threonine stress-activated kinase signal transduction molecule described herein (SEQ ID NO:3), and nucleic acid sequences coding therefor, e.g., SEQ ID NO:1 and SEQ ID NO:2, have significant potential as specific targets that can be exploited diagnostically and therapeutically for the control of pathophysiologies relating to inflammation, dysfunctional macrophages, dysfunctional endothelial cells, and related inflammatory diseases including but not limited to conditions such as atherosclerosis, asthma, allergic response, ARDS, heart failure, Atheroma and related disorders.

Differentiation, proliferation, growth arrest, or apoptosis of cells depends on the presence of appropriate cytokines and their receptors, as well as the corresponding cellular signal transduction cascades. It remains clear that stress kinase pathways, make critical contributions to transformation. In view of the positioning of raf-MEK1-Erk1/2 downstream of ras, the antiproliferative biological effect of inhibiting signal transduction in the MAP kinase pathway have significant therapeutic potential, applicable, for example, but not limited to tumours harbouring oncogenic ras. Moreover, activation of stress pathway kinases has been implicated in mediating apoptosis by agents such as TNF in model systems. Evidence regarding the involvement of intracellular signalling pathways in the maintenance of cellular survival suggests that survival and mitogenic signals can be separable and that the balance between these signals plays a key role in determining the fate of transformed cells. There are also indications that perturbation of this balance provides selective apoptosis. It would be critical to achieve optimum selectivity between pathways to achieve apoptosis promotion in tumour cells.

Unfortunately, in spite of the introduction of numerous new drugs during the last three decades, only very modest progress can be registered with regard to both cure or survival rates of cancer patients treated with anti-tumor agents. Thus, there is a need for new, more efficient and less toxic compounds. The majority of presently used anti-tumor agents interfere with the biosynthesis of nucleic acids or their intracellular function. Compounds which inhibit uncontrolled growth by interfering with mitogenic signal transduction may act as cytostatic rather than cytotoxic drugs. Furthermore, attenuation of cellular proliferation has frequently been shown to cause tissue differentiation. Finally, blockade of mitogenic stimulation in a cell can result in the inductioin of apoptosis or programmed cell death. Accordingly, the novel human serine/threonine stress-activated kinase signal transduction molecule described herein (SEQ ID NO:3), and nucleic acid sequences coding therefor, e.g. SEQ ID NO:1 and SEQ ID NO:2, have significant potential as a specific targets that can be exploited diagnostically and therapeutically to control cancer and the proliferation of tumor cells.

Activation of members of each of the MAPK pathways has been demonstrated in response to endothelin, serum, PDGF and TGFβ in various types of 'fibroblast'. Dominant negatives of ERK1 and Rac have been demonstrated, for example, to inhibit expression of a collagen promotor/reporter gene in TGFβ-stimulated 3T3 fibroblasts. Moreover, in stellate liver cells, for instance, evidence has been shown that Raf and the JNK pathway interact to control cell proliferation and collagen expression. A number of cytokines, some of which are known to activate SAPKs in cells, have been implicated in cachexia. Accordingly, the novel human serine/threonine stress-activated kinase signal transduction molecule described herein (SEQ ID NO:3), and nucleic acid sequences coding therefor, e.g. SEQ ID NO:1 and SEQ ID NO:2, have significant potential as specific targets that can be exploited diagnostically and therapeutically in the control of dysfunctional fibroblasts, including but not limited to conditions such as pathological fibrosis, and cachexia as well as other diseases manifested by dysfunctional fibroblasts.

The establishment and remodeling of blood vessels is controlled by paracrine signals, many of which are protein ligands that bind and modulate the activity of transmembrane receptor tyrosine kinases (RTKs). The basic view of RTK signaling has come from studies (performed largely in fibroblasts) of ligand-dependent autophosphorylation and activation of the branched Ras pathways. The results suggest that most RTKs are similarly coupled into the intracellular signal transduction cascade and are capable of inudcing cell proliferation. Hanahan, D., Signaling Vascular Morphogenesis and Maintenance, Science, 227:48 (1997). Angiogenic response of vascular endothelium, endothelial cell proliferation, is one of the first steps in the angiogenic process which has clearly been demonstrated to be induced by hypoxia stress. VEGF, bFGF, and EGF all have been demonstrated to upregulate MAPK in HUVEC cells. Accordingly, the novel human serine/threonine stress-activated kinase signal transduction molecule described herein (SEQ ID NO:3), and nucleic acid sequences coding therefor, e.g. SEQ ID NO:1 and SEQ ID NO:2, have significant potential as specific targets that can be exploited diagnostically and therapeutically to control angiogenesis as well as other manifestations of dysfunctional fibroblasts.

Stress-activated protein kinase (SAPK), members of the ERK family, are activated in situ by inflammatory stimuli, including tumour-necrosis factor (TNF). TNF is believed to be responsible for the development of insulin resistance associated with obesity. Exposure of cultured cells to TNFα induces insulin resistance which is believed to be mediated by the Type I TNFα receptor and intracellular signalling mechanisms. In view of the evidence that TNFα is intimately associated with the activation of Stress Activated Protein Kinases (SAPKs), the novel human serine/threonine stress-activated kinase signal transduction molecule described herein (SEQ ID NO:3), and nucleic acid sequences coding therefor, e.g. SEQ ID NO:1 and SEQ ID NO:2, have significant potential as specific targets that can be exploited diagnostically and therapeutically to control Diabetes and related disorders.

The leptin receptor belongs to the cytokine receptor superfamily of which several members have been shown to feed into SAPK pathways. Intracellular signalling pathways utilised by leptin and the potential for regulation of the leptin receptor through "cross-talk" with other signalling pathways is expected to lead to the design of novel therapeutic approaches for the treatment of obesity. Accordingly, the novel human serine/threonine stress-activated kinase signal transduction molecule described herein (SEQ ID NO:3), and nucleic acid sequences coding therefor, e.g. SEQ ID NO:1 and SEQ ID NO:2, have significant potential as specific targets that can be exploited diagnostically and therapeutically to control Obesity and related disorders.

Compounds which modulate or inactivate specific signal transduction molecules integral to specific cytosolic pathways generally have significant potential for the ability to modulate or attenuate downstream physiological responses. Accordingly, the ability to screen for compounds which modulate the activity of the native human stress-activated serine/threonine signal transduction kinase molecule described herein is of paramount importance toward the development of therapeutic agents.

Functional Constructions

The cDNA for the kinase of the present invention has been subcloned into several expression vectors for the purpose of providing recombinant protein useful for drug screen assays and for further testing the physiological role of the kinase. A dominant negative/inactive kinase mutant, for example, has been produced which will be used to further characterize the physiological role of the kinase. The cDNA has been subcloned into an expression vector in the antisense orientation to provide a tool for producing gene knock-out studies of gene function. Expression studies are performed using either constitutive or induced expression systems in mammalian cell lines. The constructs herein described are example embodiments to be used to transfect mammalian cell lines, e.g., U937 and other well-known cell lines, in order to provide recombinant protein suitable for use in drug screen assays. Constructs are contemplated for over-expressing the wild-type and/or dominant negative kinase of the present invention for characterization its physiological role including activation stimuli, identification of signal transduction pathways, identification of protein-protein interactions, as well as validation of optimal drug candiates. Down-regulation of the native signal transduction kinase molecule described herein is also contemplated using antisense expression.

A constitutive expression construct containing a coding region for the novel kinase was produced using pEBVHisA (Invitrogen Corporation). This expression construct is designed to express an N-terminal epitope tagged fusion protein containing the protein sequence:

Methionine-(Histidine)$_6$-Enterokinase protease cleavage site/Xpress™ antibody epitope—kinase protein (SEQ ID NO:3)

The SEQ ID NO:1 cDNA was excised from the pT7Blue (Novagen, Inc.) (EXAMPLE I) construct and inserted into the pEBVHisA vector using KpnI and HindIII restriction endonuclease sites at the 5' end and 3' end, respectively.

Protein expression using the SEQ ID NO:1 cDNA/pEBVHisA construct encodes a His$_6$-Xpress Ab epitope-Kinase fusion protein. Some characteristics of the chimeric molecule include, 482 amino acids, molecular weight 53669.60 daltons, isoelectric point of 5.384, and –15.707 net charge at PH 7.0.

An inducible expression construct containing a coding region for the novel kinase was produced using pIND ecdysone inducible expression vector (Invitrogen Corporation). This expression construct is designed to express an N-terminal epitope tagged fusion protein containing the protein sequence:

Methionine-(Histidine)$_6$-Enterokinase protease cleavage site/Xpress™ antibody epitope—kinase protein (SEQ ID NO:3)

The SEQ ID NO:1 cDNA was excised from the pT7Blue (Novagen, Inc.) (EXAMPLE I) construct and inserted into the pIND vector. The The H$_6$-Xpress Ab epitope-SEQ ID NO:1 insert was excised using ApaLI and XbaI restriction endonuclease sites at the 5' end and 3' end, respectively. The ApaLI site was filled-in using Klenow DNA polymerase to produce a blunt end. The insert was then ligated into the EcoRV and XbaI restriction endonuclease sites of the pIND vector.

A dominant negative/inactive kinase mutant version of the kinase described herein was produced by changing the lysine at SEQ ID NO:3 position 53 to an arginine. See FIG. 8. This mutation has been shown to produce inactive and/or dominant negative kinases for numerous other serine/threonine kinases. See, e.g., Hanks, S. K., et al. Science, 241:42 (1988). The mutation was introduced into the SEQ ID NO:1/pT7Blue construct using the Quick Change Site Directed Mutagenesis Kit (Stratagene) and the oligonucleotides shown in FIG. 8 (SEQ ID NO:6 and SEQ ID NO:7). This produced the K53R/pT7Blue construct.

A constitutive expression construct containing a coding region for the novel kinase K53R dominant negative mutant was produced using pEBVHisA (Invitrogen Corporation). This expression construct is designed to express an N-terminal epitope tagged fusion protein containing the following protein sequence:

Methionine-(Histidine)$_6$-Enterokinase protease cleavage site/Xpres™ antibody epitope—K53R dominant negative mutant kinase protein The SEQ ID NO:1/K53R cDNA was excised from the K53R/pT7Blue construct and inserted into the pEBVHisA vector using KpnI and HindIII restriction endonuclease sites at the 5' end and 3' end, respectively.

Generally Acceptable Vectors

In accordance with the present invention, polynucleotide sequences which encode the novel kinase, fragments of the polypeptide, fusion proteins or functional equivalents thereof may be used in recombinant DNA molecules that direct the expression of the signal transduction molecule in appropriate host cells. Due to the inherent degeneracy of the genetic code, other DNA sequences which encode substantially the same or a functionally equivalent amino acid sequence, may be used to clone and express the novel human signal-transduction kinase. As will be understood by those of skill in the art, it may be advantageous to produce novel kinase-encoding nucleotide sequences possessing non-naturally occurring codons.

Specific initiation signals may also be required for efficient translation of a signal-transduction kinase sequence. These signals include the ATG initiation codon and adjacent sequences. In cases where the novel kinase, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic.

Cloned signal transduction kinaseDNA obtained through the methods described herein may be recombinantly expressed by molecular cloning into an expression vector containing a suitable promoter and other appropriate transcription regulatory elements, and transferred into prokaryotic or eukaryotic host cells to produce the kinase polypeptide. Techniques for such manipulations are fully described in Sambrook, J., et al., Molecular Cloning Second Edition, Cold Spring Harbor Press (1990), and are well known in the art.

Expression vectors are described herein as DNA sequences for the transcription of cloned copies of genes and the translation of their mRNAs in an appropriate host cell. Such vectors can be used to express nucleic acid sequences in a variety of hosts such as bacteria, bluegreen algae, plant cells, insect cells, fungal cells, human, and animal cells. Specifically designed vectors allow the shuttling of DNA between hosts such as bacteria-yeast, or bacteria-animal cells, or bacteria-fungal cells, or bacteria-invertebrate cells.

A variety of mammalian expression vectors may be used to express the recombinant human kinase molecule disclosed herein in mammalian cells. Commercially available mammalian expression vectors which are suitable for recombinant expression, include but are not limited to, pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565), pLXIN and pSIR (CLONTECH), pIRES-EGFP (CLONTECH). INVITROGEN corporation provides a wide variety of commercially available mammalian expression vector/systems which can be effectively used with the present invention. INVITROGEN, Carlsbad, Calif. See, also, PHARMINGEN products, vectors and systems, San Diego, Calif.

Baculoviral expression systems may also be used with the present invention to produce high yields of biologically active protein. Vectors such as the CLONETECH, BacPak™ Baculovirus expression system and protocols are preferred which are commercially available. CLONTECH, Palo Alto, Calif. Miller, L. K., et al., Curr. Op. Genet. Dev. 3:97 (1993); O'Reilly, D. R., et al., *Baculovirus Expression Vectors: A Laboratory Manual*, 127. Vectors such as the INVITROGEN, MaxBac™ Baculovirus expression system, insect cells, and protocols are also preferred which are commercially available. INVITROGEN, Carlsbad, Calif.

Example Host Cells

Host cells transformed with a nucleotide sequence which encodes the human kinase of the present invention may be cultured under conditions suitable for the expression and recovery of the encoded protein from cell culture. Particularly preferred embodiments of the present invention are host cells transformed with a purified polynucleotide comprising a nucleic acid sequence encoding the polypeptide having the sequence substantially as depicted in SEQ ID NO:3 or a biologically active fragment thereof. Cells of this type or preparations made from them may be used to screen for pharmacologically active modulators of the novel human signal-transduction kinase activity.

Eukaryotic recombinant host cells are especially preferred. Examples include but are not limited to yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616),BS-C-1 (ATCC CCL 26) and MRC-5 (ATCC CCL 171).

The expression vector may be introduced into host cells expressing the novel kinase via any one of a number of techniques including but not limited to transformation, transfection, lipofection, protoplast fusion, and electroporation. Commercially available kits applicable for use with the present invention for hererologous expression, including well-characterized vectors, transfection reagents and conditions, and cell culture materials are well-established and readily available. CLONTECH, Palo Alto, Calif.; INVITROGEN, Carlsbad, Calif.; PHARMINGEN, San Diego, Calif.; STRATAGENE, La Jolla, Calif. The expression vector-containing cells are clonally propagated and individually analyzed to determine the level of novel kinase protein production. Identification of host cell clones which express the novel kinase may be performed by several means, including but not limited to immunological reactivity with antibodies described herein, and/or the presence of host cell-associated specific kinase activity, and/or the ability to covalently cross-link specific substrate to the novel kinase with the bifunctional cross-linking reagent disuccinimidyl suberate or similar cross-linking reagents.

The signal transduction molecule of the present invention may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals (Porath, J., Protein Exp. Purif. 3:263 (1992)), protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and TMP is useful to facilitate purification.

Systems such as the CLONTECH, TALON™ nondenaturing protein purification kit for purifying 6xHis-tagged proteins under native conditions and protocols are preferred which are commercially available. CLONTECH, Palo Alto, Calif.

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a nascent form of the protein may also be important for correct insertion, folding and/or function. Different host cells such as CHO, HeLa, MDCK, 293, WI38, NIH-3T3, HEK293 etc., have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express the novel kinase may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

The human kinase can be produced in the yeast *S. cerevisiae* following the insertion of the optimal cDNA cistron into expression vectors designed to direct the intracellular or extracellular expression of the heterologous protein. In the case of intracellular expression, vectors such as EmBLyex4 or the like are ligated to the beta subunit cistron. See, e.g., Rinas, U., et al., Biotechnology, 8:543 (1990); Horowitz, B., et al., J. Biol. Chem., 265:4189 (1989). For extracellular expression, the kinase cistron is ligated into yeast expression vectors which may employ any of a series of well-characterized secretion signals. The levels of expressed novel kinase are determined by the assays described herein.

A variety of protocols for detecting and measuring the expression of the novel kinase, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes may be employed. Well known competitive binding techniques may also be employed. See, e.g., Hampton, R., et al. (1990), Serological Methods—a Laboratory Manual, APS Press, St Paul Minn.; Maddox, D. E., et al., J. Exp. Med. 158:1211.

Yeast 2-Hybrid System

In another embodiment of the invention, a nuleic acid sequence which encodes a human signal-transduction kinase molecule substantially as depicted in SEQ ID NO:3 or a biologically active fragment thereof may be ligated to a heterologous sequence to encode a fusion protein. For example, for screening compounds for modulation of biological activity, it may be useful to encode a chimeric kinase molecule as described herein for expression in hererologous host cells. Chimeric constructs may also be used to express a 'bait', according to methods well known using a yeast two-hybrid system, to identify accessory native peptides that may be associated with the novel human signal-transduction kinase molecule described herein. Fields, S., et al., Trends Genet., 10:286 (1994); Allen, J. B., et al., TIBS, 20:511 (1995). A yeast two-hybrid system has been described wherein protein:protein interactions can be detected using a yeast-based genetic assay via reconstitution of transcriptional activators. Fields, S., Song, O., Nature 340:245 (1989). The two-hybrid system used the ability of a pair of interacting proteins to bring a transcription activation domain into close proximity with a DNA-binding site that regulates the expression of an adjacent reporter gene. Commercially available systems such as the CLONTECH, Matchmaker™ systems and protocols may be used with the present invention. CLONTECH, Palo Alto, Calif. See also, Mendelsohn, A. R., Brent, R., Curr. Op. Biotech., 5:482 (1994); Phizicky. E. M., Fields, S., Microbiological Rev., 59(1):94 (1995); Yang, M., et al., Nucleic Acids Res., 23(7):1152 (1995); Fields, S., Sternglanz, R., TIG, 10(8) :286 (1994); and U.S. Pat. No. 5,283,173, System to Detect Protein-Protein Interactions, and U.S. Pat. No. 5,468,614, which are incorporated herein by reference.

Antibodies

Monospecific antibodies to the signal transduction kinase polypeptide of the present invention are purified from mammalian antisera containing antibodies reactive against the polypeptide or are prepared as monoclonal antibodies reactive with signal transduction kinase polypeptide using the technique of Kohler and Milstein, Nature, 256:495 (1975). Mono-specific antibody as used herein is defined as a single antibody species or multiple antibody species with homogenous binding characteristics for the novel signal transduction kinase. Homogenous binding as used herein refers to the ability of the antibody species to bind to a specific antigen or epitope, such as those associated with the novel signal transduction kinase, as described. Novel signal transduction kinase specific antibodies are raised by immunizing animals such as mice, rats, guinea pigs, rabbits, goats, horses and the like, with rabbits being preferred, with an appropriate concentration of the human signal transduction kinase either with or without an immune adjuvant.

Preimmune serum is collected prior to the first immunization. Each animal receives between about 0.1 mg and about 1000 mg of signal transduction kinase polypeptide associated with an acceptable immune adjuvant. Such acceptable adjuvants include, but are not limited to, Freund's complete, Freund's incomplete, alum-precipitate, water in oil emulsion containing Corynebacterium parvum and tRNA. The initial immunization consists of signal transduction kinase polypeptide in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with the signal transduction kinase polypeptide are prepared by immunizing inbred mice, preferably Balb/c, with the signal transduction kinase polypeptide. The mice are immunized by the IP or SC route with about 0.1 mg to about 10 mg, preferably about 1 mg, of signal transduction kinase polypeptide in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 mg of signal transduction kinase polypeptide in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 molecular weight, at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using the human signal transduction kinase polypeptide as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of the anti-human kinase polypeptide mAb is carried out by growing the hydridoma in DMEM containing about 2% fetal calf serum to obtain sufficient quantities of the specific mAb. The mAb are purified by techniques known in the art.

Diagnostic Assays

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar diagnostic assays are used to detect the presence of the novel signal transduction kinase polypeptide in body fluids or tissue and cell extracts.

Diagnostic assays using the human signal-transduction kinase polypeptide specific antibodies are useful for the diagnosis of conditions, disorders or diseases characterized by abnormal expression of the signal-transduction kinase polypeptide or expression of genes associated with abnormal cell growth. Diagnostic assays for the signal-transduction kinase polypeptide of this invention include methods utilizing the antibody and a label to detect the human kinase polypeptide in human body fluids, cells, tissues or sections or extracts of such tissues. The polypeptides and antibodies of the present invention may be used with or without modification. Frequently, the polypeptides and antibodies will be labeled by joining them, either covalently or noncovalently, with a reporter molecule, a myriad of which are well-known to those skilled in the art.

A variety of protocols for measuring the kinase polypeptide, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on the human signal-transduction kinase polypeptide is preferred, but a competitive binding assay may be employed. These assays are described, among other places, in Maddox, D. E. et al., J. Exp. Med. 158:1211 (1983); Sites, D. P., et al., *Basic and Clinical Immunology*, Ch.22, 4th Ed., Lange Medical Publications, Los Altos, Calif. (1982); U.S. Pat. Nos. 3,654,090, No. 3,850,752; and No. 4,016,043.

In order to provide a basis for the diagnosis of disease, normal or standard values for the human signal-transduction kinase polypeptide expression must be established. This is accomplished by combining body fluids or cell extracts taken from normal subjects, either animal or human, with antibody to the human kinase polypeptide under conditions suitable for complex formation which are well known in the art. The amount of standard complex formation may be quantified by comparing it with a dilution series of positive controls where a known amount of antibody is combined with known concentrations of purified human signal-transduction kinase polypeptide. Then, standard values obtained from normal samples may be compared with values obtained from samples from subjects potentially affected by a disorder or disease related to the human kinase polypeptide expression. Deviation between standard and subject values establishes the presence of the disease state.

Kits containing human stress-activated signal-transduction kinase nucleic acid, antibodies to a kinase polpeptide, or protein may be prepared. Such kits are used to detect heterologous nucleic acid which hybridizes to kinase nucleic acid, or to detect the presence of protein or peptide fragments in a sample. Such characterization is useful for a variety of purposes including, but not limited to, forensic analyses and epidemiological studies.

The DNA molecules, RNA molecules, recombinant protein and antibodies of the present invention may be used to screen and measure levels of the novel kinase DNA, RNA or protein. The recombinant proteins, DNA molecules, RNA molecules and antibodies lend themselves to the formulation of kits suitable for the detection and typing of the human signal-transduction kinase. Such a kit would comprise a compartmentalized carrier suitable to hold in close confinement at least one container. The carrier would further comprise reagents such as recombinant human kinase or anti-kinase antibodies suitable for detecting the novel kinase. The carrier may also contain a means for detection such as labeled antigen or enzyme substrates or the like.

Polynucleotide sequences which encode the novel kinase may be used for the diagnosis of conditions or diseases with which the expression of the novel human stress-activated kinase is associated. For example, polynucleotide sequences encoding the signal-transduction molecule may be used in hybridization or PCR assays of fluids or tissues from biopsies to detect expression of the kinase. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits. Such assays may also be used to evaluate the efficacy of a particular therapeutic treatment regime in animal studies, in clinical trials, or in monitoring the treatment of an individual patient. Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

Polynucleotide sequences which encode the novel kinase may also be employed in analyses to map chromosomal locations, e.g., screening for functional association with disease markers. Moreover the sequences described herein are contemplated for use to identify human sequence polymorphisms and possible association with disease as well as analyses to select optimal sequence from among possible polymorphic sequences for the design of compounds to modulate the biological activity. Furthermore the sequences are contemplated as screening tools for use in the identification of appropriate human subjects and patients for therapeutic clinical trials.

Purification Via Affinity Columns

It is readily apparent to those skilled in the art that methods for producing antibodies may be utilized to produce antibodies specific for the human kinase polypeptide fragments, or the full-length nascent human kinase polypeptide. Specifically, it is readily apparent to those skilled in the art that antibodies may be generated which are specific for the fully functional receptor or fragments thereof.

Kinase polypeptide antibody affinity columns are made by adding the antibodies to Affigel-10 (Biorad), a gel support which is activated with N hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) with appropriate detergent and the cell culture supernatants or cell extracts containing human signal-transduction kinase polypeptide made using appropriate membrane solubilizing detergents are slowly passed through the column. The column is then washed with phosphate buffered saline/detergent until the optical density falls to background, then the protein is eluted with 0.23M glycine-HCl (pH 2.6)/detergent. The purified human signal-transduction kinase polypeptide is then dialyzed against phosphate buffered saline/detergent.

Recombinant kinase molecules can be separated from other cellular proteins by use of an immunoaffinity column made with monoclonal or polyclonal antibodies specific for full length nascent human kinase polypeptide, or polypeptide fragments of the kinase molecule.

Human kinase polypeptides described herein may be used to affinity purify biological effectors from native biological materials, e.g. disease tissue. Affinity chromatography techniques are well known to those skilled in the art. A human signal-transduction kinase peptide described herein or an effective fragment thereof, is fixed to a solid matrix, e.g. CNBr activated Sepharose according to the protocol of the supplier (Pharmacia, Piscataway, N.J.), and a homogenized/buffered cellular solution containing a potential molecule of interest is passed through the column. After washing, the column retains only the biological effector which is subsequently eluted, e.g., using 0.5M acetic acid or a NaCl gradient.

Antisense Molecules

The cDNA sequence SEQ ID NO:1 provided herein, may be used in another embodiment of the invention to study the physiological relevance of the novel human signal-transduction kinase in cells, especially cells of hematopoietic origin, by knocking out the endogenous gene by use of anti-sense constructs.

To enable methods of down-regulating expression of the novel human kinase of the present invention in mammalian cells, an example antisense expression construct containing the complement DNA sequence (5'→3' is shown in FIG. 7 (SEQ ID NO:5)) to the novel kinase cDNA was produced using the pREP10 vector (Invitrogen Corporation). The SEQ ID NO:1 cDNA was excised from the pT7Blue (Novagen, Inc.) construct and inserted into the pREP10 vector using KpnI and HindIII restriction endonuclease sites at the 5' end and 3' end, respectively. This places the SEQ ID NO:1 cDNA in an anti-sense orientation with respect to the promoter and is expected to express an antisense mRNA transcript. Transcripts are expected to inhibit translation of the wild-type kinase mRNA in cells transfected with this construct. Oligomers of 12–21 nucleotides are most preferred in the practice of the present invention, particularly oligomers of 12–18 nucleotides. Transcript are, in principle, effective for inhibiting translation of the transcript, and capable of inducing the effects herein described. Translation is most effectively inhibited by blocking the mRNA at a site at or near the initiation codon. Thus, oligonucleotides complementary to the 5' -terminal region of the human kinase mRNA transcript are preferred. Secondary or tertiary structure which might interfere with hybridization is minimal in this region. Moreover, sequences that are too distant in the 3' direction from the initiation site can be less effective in hybridizing the mRNA transcripts because of a "read-through" phenomenon whereby the ribosome appears to unravel the antisense/sense duplex to permit translation of the message. Oligonucleotides which are complementary to and hybridizable with any portion of the novel human signal-transduction kinase mRNA are contemplated for therapeutic use U.S. Pat. No. 5,639,595, Identification of Novel Drugs and Reagents, issued Jun. 17, 1997, wherein methods of identifying oligonucleotide sequences that display in vivo activity are thoroughly described, is herein incorporated by reference. Expression vectors containing random oligonucleotide sequences derived from previously known polynucleotides are transformed into cells. The cells are then assayed for a phenotype resulting from the desired activity of the oligonucleotide. Once cells with the desired phenotype have been identified, the sequence of the oligonucleotide having the desired activity can be identified. Identification may be accomplished by recovering the vector or by polymerase chain reaction (PCR) amplification and sequencing the region containing the inserted nucleic acid material.

Nucleotide sequences that are complementary to the novel signal-transduction kinase polypeptide encoding polynucleotide sequence can be synthesized for antisense therapy. These antisense molecules may be DNA, stable derivatives of DNA such as phosphorothioates or methylphosphonates, RNA, stable derivatives of RNA such as 2'-O-alkylRNA, or other oligonucleotide mimetics. U.S. Pat. No. 5,652,355, Hybrid Oligonucleotide Phosphorothioates, issued Jul. 29, 1997, and U.S. Pat. No. 5,652,356, Inverted Chimeric and Hybrid Oligonucleotides, issued Jul. 29, 1997, which describe the synthesis and effect of physiologically-stable antisense molecules, are incorporated by reference. Signal-transduction kinase antisense molecules may be introduced into cells by microinjection, liposome encapsulation or by expression from vectors harboring the antisense sequence. Antisense therapy may be particularly useful for the treatment of diseases where it is beneficial to reduce the signal-transduction kinase activity.

Gene Therapy

A human signal-transduction kinase polypeptide described herein may administered to a subject via gene therapy. Moreover, a polypeptide of the present invention may be delivered to the cells of target organs in this manner. Conversely, signal-transduction kinase polypeptide antisense gene therapy may be used to reduce the expression of the polypeptide in the cells of target organs. The human signal-transduction kinase polypeptide coding region can be ligated into viral vectors which mediate transfer of the kinase polypeptide DNA by infection of recipient host cells. Suitable viral vectors include retrovirus, adenovirus, adeno-associated virus, herpes virus, vaccinia virus, polio virus and the like. See, e.g., U.S. Pat. No. 5,624,820, Episomal Expression Vector for Human Gene Therapy, issued Apr. 29, 1997. Nucleic acid coding regions of the present invention are incorporated into effective eukaryotic expression vectors, which are directly administered or introduced into somatic cells for gene therapy (a nucleic acid fragment comprising a coding region, preferably mRNA transcripts, may also be administered directly or introduced into somatic cells). See, e.g., U.S. Pat. No. 5,589,466, issued Dec. 31, 1996. Such nucleic acids and vectors may remain episomal or may be incorporated into the host chromosomal DNA as a provirus or portion thereof that includes the gene fusion and appropriate eukaryotic transcription and translation signals, i.e, an effectively positioned RNA polymerase promoter 5' to the transcriptional start site and ATG translation initiation codon of the gene fusion as well as termination codon(s) and transcript polyadenylation signals effectively positioned 3' to the coding region. Alternatively, the human signal-transduction kinase polypeptide DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo, as well as in vivo human signal-transduction kinase polypeptide gene therapy according to established methods in this art.

Screening Assays

The present invention is also directed to methods for screening for compounds which modulate the expression of DNA or RNA encoding the novel human kinase polypeptide, as well as the function of the human signal-transduction kinase polypeptide in vivo. Compounds which modulate these activities may be DNA, RNA, peptides, proteins, or non-proteinaceous organic molecules. Compounds may modulate by increasing or attenuating the expression of DNA or RNA encoding the human signal-transduction kinase polypeptide, or the function thereof. Compounds that modulate the expression of DNA or RNA encoding the human signal-transduction kinase polypeptide or the function of the polypeptide may be detected by a variety of assays. The assay may be a simple "yes/no" assay to determine whether there is a change in expression or function. The assay may be made quantitative by comparing the expression or function of a test sample with the levels of expression or function in a standard sample.

The human signal-transduction kinase described herein, its immunogenic fragments or oligopeptides can be used for screening therapeutic compounds in any of a variety of drug screening techniques. The fragment employed in such a test may be free in solution, affixed to a solid support, borne on a cell surface, or located intracellularly. The abolition of activity or the formation of binding complexes, between the human signal-transduction kinase polypeptide and the agent being tested, may be measured. Accordingly, the present invention provides a method for screening a plurality of compounds for specific binding affinity with the human signal-transduction kinase polypeptide or a fragment thereof, comprising providing a plurality of compounds; combining the human signal-transduction kinase polypeptide of the present invention or a fragment thereof with each of a plurality of compounds for a time sufficient to allow binding under suitable conditions; and detecting binding of the kinase polypeptide, or fragment thereof, to each of the plurality of compounds, thereby identifying the compounds which specifically bind the human signal-transduction kinase polypeptide.

Methods of identifying compounds that modulate the activity of a human signal-transduction kinase polypeptide are generally preferred, which comprise combining a candidate compound modulator of a human signal-transduction kinase activity with a polypeptide of a human signal-transduction kinase having the sequence substantially as depicted in SEQ ID NO:3, and measuring an effect of the candidate compound modulator on the kinase activity.

Methods of identifying compounds that modulate the activity of a human signal-transduction kinase, are also preferred which comprise combining a candidate compound modulator of a human signal-transduction kinase activity with a host-cell expressing the polypeptide of a human signal-transduction kinase molecule having the sequence substantially as depicted in SEQ ID NO:3, and measuring an effect of the candidate compound modulator on the kinase activity. Preferred cellular assays of for inhibitors of the kinase fall into two general categories: 1) direct measurement of the kinase activity, and 2) measurement of a downstream events in the signaling cascade. These methods can employ the endogenous kinase, or the overexpressed recombinant kinase.

In order to measure the cellular activity of the kinase, the source may be a whole cell lysate, prepared by one to three freeze-thaw cycles in the presence of standard protease inhibitors. Alternatively, the kinase may be partially or completely purified by standard protein purification methods. Finally, the kinase may be purified by affinity chromatography using specific antibody for the C terminal regulatory domain described herein or by ligands specific for the epitope tag engineered into the recombinant kinase moreover described herein. The kinase preparation may then be assayed for activity as described, for example, in Example II.

A filter assay based on the protocol of Reuter et al. (1995) is also used to screen for compounds which modulate the activity of the novel kinase described herein: Starting with MBP coated 96-well FlashPlates® (NEN™ Life Science Products) reaction buffer (3×kinase reaction buffer (KRB) contains: 60 mM HEPES (pH 7.5), 30 mM magnesium acetate, 0.15 mM ATP, 3 mM DTT, 0.03 mM sodium orthovanadate) is added, 0.25 $\mu$Ci [$\gamma^{33}$P]-ATP at a concentration no greater than 1 $\mu$g/ml, (determined by titration of individual enzyme preparations for a concentration that allows kinetic determinations over a 1 hour time course of the human kinase) of the human kinase are added to each well and incubated 1 hour at 30° C. in the presence or absence of 10 $\mu$M test compound. Total reaction volume is 100 $\mu$L. The reaction is stopped by the addition of EDTA (pH 7.0) to a final concentration of 80 mM. The samples are centrifuged and 50 $\mu$L of the supernatant spotted on p81 cation-exchange filter paper (Whatman, No. 3698 915). The filters are then washed 3 times in 200 mL of 180 mM $H_3PO_4$ (5–10 min each), and once in 200 mL of 96% ethanol. After air drying the filters, radioactivity is determined by Cerenkov counting in a scintillation counter. Compounds which inhibit kinase activity $\geq$50 percent at 10 $\mu$M are are indicated by a >50% reduction in scintillation counts. Specificity and selectivity studies is determined by titration of inhibitory compounds to determine the $IC_{50}$ (or other standard quantitation well known in the art for comparison) and by the substitution of other kinases in the assay. For example, determination of relative inhibitory activity of the kinase in comparison to recombinant SOK-1, expressed and isolated in a similar manner, assayed under similar conditions, provides selectivity data. Reuter, C. W. M., Catling, A. D. and Weber, M. J., Immune Complex Kinase Assays for Mitogen-Activated Protein Kinase and MEK, Methods In Enzymology, 255:245 (1995).

To evaluate the ability of a candidate agent to inhibit human tumor growth, human tumor cells are injected into SCID mice (severe combined immunodeficiency) to form palpable tumor masses. The effects of an candidate agent in inhibiting tumor growth can be determined as follows. Approximately 1×10$^7$ cells of the CCL 221 cell line (ATCC, Rockville, Md.), a human ras-dependent colon adenocarcinoma cell line, is suspended in 100 mu l DMEM and injected subcutaneously into SCID mice, such that two tumors per mouse are formed. SCID mice receive CCL 221 cells and the tumors are grown for 7 days without treatment; on the 7th day (Day 0) tumor maximal diameters and animal weights are recorded and the mean tumor size for the mice is determined. On Day 1 (eight days following tumor cell injection), treatment of the mice with candidate agent or vehicle alone is begun. One group of the mice (controls) are injected intraperitoneally with 0.2 ml of vehicle and a second group of mice received agent by intraperitoneal injection. Various doses of agent can be tested in separate groups of mice. On Day 7 and Day 14, animal weight and maximal tumor diameter is measured. Average maximal tumor size for each group on Day 0, Day 7, and Day 14 are compared Day 14, one high dose animal was followed for an additional to determined whether the agent produces a dose-dependent inhibition of tumor growth. Toxicity effects can be examined by tracking mice weight and by harvesting lungs, livers, and spleens of the animals for histologically staining.

Compounds which are identified generally according to methods descibed and referenced herein that modulate the activity of a human signal-transduction kinase comprised of the sequence substantially as depicted in SEQ ID NO:3 are especially preferred embodiments of the present invention.

An especially preferred embodiment of the present invention is a method for treatment of a patient in need of such treatment for a condition which is mediated by the human signal-transduction kinase described herein comprising administration of a therapeutically effective amount of a human signal-transduction kinase modulating compound.

PCR Diagnostics

The nucleic acid sequence, oligonucleotides, fragments, portions or antisense molecules thereof, may be used in diagnostic assays of body fluids or biopsied tissues to detect the expression level of the novel human signal-transduction kinase molecule. For example, sequences designed from the cDNA sequence SEQ ID NO:1 or sequences comprised in SEQ ID NO:2 can be used to detect the presence of the mRNA transcripts in a patient or to monitor the modulation of transcripts during treatment.

One method for amplification of target nucleic acids, or for later analysis by hybridization assays, is known as the polymerase chain reaction ("PCR") or PCR technique. The PCR technique can be applied to detect sequences of the invention in suspected samples using oligonucleotide primers spaced apart from each other and based on the genetic sequence, e.g., SEQ ID NO:1, set forth herein. The primers are complementary to opposite strands of a double stranded DNA molecule and are typically separated by from about 50 to 450 nucleotides or more (usually not more than 2000 nucleotides). This method entails preparing the specific oligonucleotide primers followed by repeated cycles of target DNA denaturation, primer binding, and extension with a DNA polymerase to obtain DNA fragments with the expected length based on the primer spacing. One example embodiment of the present invention is a diagnostic composition for the identification of a polynucleotide sequence comprising the sequence substantially as depicted in SEQ ID NO:2 comprising the PCR primers substantially as depicted in SEQ ID NO:8 and SEQ ID NO:9. The degree of amplification of a target sequence is controlled by the number of cycles that are performed and is theoretically calculated by the simple formula 2n where n is the number of cycles. See, e.g., Perkin Elmer, PCR Bibliography, Roche Molecular Systems, Branchburg, N.J.; CLONTECH products, Palo Alto, Calif.; U.S. Pat. No. 5,629,158, Solid Phase Diagnosis of Medical Conditions, issued May 13, 1997.

Compositions

Pharmaceutically useful compositions comprising the novel human kinase polypeptide DNA, human kinase polypeptide RNA, antisense sequences, or the human kinase polypeptide, or variants and analogs which have the human kinase activity or otherwise modulate its activity, may be formulated according to known methods such as by the admixture of a pharmaceutically acceptable carrier. Examples of such carriers and methods of formulation may be found in *Remington's Pharmaceutical Sciences* (Maack Publishing Co, Easton, Pa.). To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose human signal-transduction kinase polypeptide related disorders. The effective amount may vary according to a variety of factors such as the individual's condition, weight, sex and age. Other factors include the mode of administration.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as *Remington's Pharmaceutical Sciences*.

Pharmaceutical compositions suitable for use in the present invention include compositions wherein the active ingredients are contained in an effective amount to achieve the intended purpose. The determination of an effective dose is well within the capability of those skilled in the art. The therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans. A therapeutically effective dose refers to that amount of protein or its antibodies, antagonists, or inhibitors which ameliorate the symptoms or condition. The exact dosage is chosen by the individual physician in view of the patient to be treated.

Compounds identified according to the methods disclosed herein may be used alone at appropriate dosages defined by routine testing in order to obtain optimal modulation of a signal-transduction kinase, or its activity while minimizing any potential toxicity. In addition, co-administration or sequential administration of other agents may be desirable.

The pharmaceutical compositions may be provided to the individual by a variety of routes such as subcutaneous, topical, oral and intramuscular. Administration of pharmaceutical compositions is accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present invention also has the objective of providing suitable topical, oral, systemic and parenteral pharmaceutical formulations for use in the novel methods of treatment of the present invention. The compositions containing compounds identified according to this invention as the active ingredient for use in the modulation of signal-transduction kinase can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a signal-transduction kinase modulating agent.

The daily dosage of the products may be varied over a wide range from 0.01 to 1,000 mg per adult human/per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. Even more particularly, the range varies from about 0.05 to about 1 mg/kg. Of course the dosage level will vary depending upon the potency of the particular compound. Certain compounds will be more potent than others. In addition, the dosage level will vary depending upon the bioavailability of the compound. The more bioavailable and potent the compound, the less compound will need to be administered through any delivery route, including but not limited to oral delivery. The dosages of the human signal-transduction kinase modulators are adjusted when combined to achieve desired effects. On the other hand, dosages of these various agents may be independently optimized and combined to achieve a synergistic result wherein the pathology is reduced more than it would be if either agent were used alone. Those skilled in the art will employ different formulations for nucleotides than for proteins or their inhibitors. Similarly, delivery of polynucleotides or polypeptides will be specific to particular cells and conditions.

EXAMPLES

Example I

Sequence Construction, Cloning, Expression and Purification

The novel human kinase described herein was identified after the assembly of expressed sequence tags (ESTs) from from the Incyte LIFSEQ database. Initial identification of these ESTs was performed by basic local alignment search tool (BLAST) analysis of the database using the kinase subdomain VIB sequence HRDLKPENILLD previously decribed. This highly conserved sequence tends to be specific for serine/threonine kinases. Altschul, Stephen F., et al., Basic Local Alignment Search Tool, J. Mol. Biol., 215:403 (1990); Altschul, Stephen F., et al., A Protein Alignment Scoring System Sensitive at all Evolutionary Distances, J. Mol. Evol., 36:290 (1993); Altschul, Stephen F., et al., Issues in Searching Molecular Sequence Databases, Nature Genetics, 6:119 (1994).

Oligonucleotide primers, sense 5'GAGCGCCATGGCT-CACTCC3' (SEQ ID NO:8) and antisense 5'GGAGT-CAGCGAAGGCTCTCG3' (SEQ ID NO:9), were designed based on the predicted sequence to the novel human kinase and were used to amplify nucleic acid sequence pertaining to the novel human kinase from human brain cDNA (Clontech) and human U937 cell cDNA using Taq polymerase. Clones were sequenced (ABI PRISM™ Dye Terminator Cycle sequencing on ABI PRISM™ 377 automated sequencer). This yielded a single cDNA species of the sequence SEQ ID NO:1, validating the electronic assembly of the cDNA. The PCR products were ligated into the pT7Blue vector (Novagen, Inc.) and used to transform NovaBlue competent cells (Novagen, Inc.). Plasmids were prepared from positive clones for sequencing. A clone was found to have sequence identical to the electronic contig for the new kinase molecule, nucleic acid SEQ ID NO:1. The 2322 basepair (bp) sequence was found to contain a 1293 bp open reading frame (ORF) with a Kozak initiation sequence at the start methionine. Translation of the ORF resulted in a 431 amino acid protein which contains all 11 homologous domains found in eukaryotic protein kinases. The novel kinase has 69.7 percent identity to the Ste20/oxidant stress response kinase-1 (SOK-1) described by Pombo et al. (1996). The protein also has a predicted molecular weight of 47,919 daltons, an isoelectric point of 5.24 and a net charge of −12.68.

The pT7Blue plasmid containing SEQ ID NO:1 was gel purified, restriction digested with EcoRI/Sal I, and ligated into the multiple cloning site of the GST gene fusion vector pGEX-5X-2 (Pharmacia Biotech, Inc.). The resultant construct was used to transform NovaBlue competent E. coli cells for maintenance and BL21 competent cells (Novagen, Inc.) for protein expression. GST fusion clones were screened for the incorporation of the correct sequence. A single BL21 clone was isolated for protein expression. This clone was grown overnight in 10 mL Lennox L broth (LB broth) and seeded into 1 liter LB broth and grown at 37° C. with agitation to an $A_{600}$ of 1.0–2.0. Expression of the GST/novel kinase fusion protein was induced by adding 100 $\mu$M isopropylthio-β-galactoside, incubation for 2 more hours. Following incubation, the culture was centrifuged 1500×g, 10 min, 4° C. and resuspended in 50 mL phosphate buffered saline (PBS) containing Complete™ Protease Inhibitor Cocktail (Boehringer Mannheim GmbH). Cells were then lysed by sonication on ice. Triton X-100 was added to the sonicate to a final concentration of 1% to aid in the solubilization of the fusion protein. Cellular debris was removed by centrifugation (12,000×g, 4° C.).

The kinase molecule was purified by the addition of Glutathione Sepharose 4B beads (Pharmacia) at a concentration of 1 ml of a 50% slurry in PBS per 50 mL of lysate. The suspension was incubated for 30 minutes at room temperature with gentle agitation, centrifuged (500×g, 5 min, 4° C.) and washed three times with PBS containing protease inhibitors. Finally, the beads were sedimented by centrifugation, resuspended in 1mL elution buffer (10 mM reduced glutathione in 50 mM Tris-HCl, pH 8.0 with protease inhibitors) and incubated 10 minutes at room temperature to remove the fusion protein from the beads. Beads were spun out (500×g, 5 min) and the GST/kinase fusion was stored in aliquots at −20° C. until needed.

Example II

Assay for Human Kinase Activity

The recombinant, Glutathionine S-transferase (GST)/novel human kinase fusion was constructed by digesting a pT7Blue vector (Novagen, Inc.) containing SEQ ID NO:1 with EcoRI/Sal I, and subsequent ligation into the multiple cloning site of the GST gene fusion vector pGEX-5X-2 (Pharmacia Biotech, Inc.). The resultant construct was used to transform BL21 competent cells (Novagen, Inc.) for protein expression.

Recombinant, purified GST/kinase (10 $\mu$L) was added to 20 $\mu$g myelin basic protein (MBP) in 10 $\mu$L of a 3×kinase reaction buffer (KRB) containing: 60 mM HEPES (pH 7.5), 30 mM magnesium acetate, 0.15 mM ATP, 3 mM DTT, 0.03 mM sodium orthovanadate. The reaction was started by the addition of 5 $\mu$Ci [γ-$^{32}$P] ATP (10 $\mu$L). Samples were incubated for 5 minutes at 30° C. and the reaction was stopped by addition of 4×Laemmli sample buffer. Proteins were separated on 12% Tris/glycine SDS gels, stained with Coomassie blue, dried and exposed to autoradiograph film.

Results of an autoradiographic assay for the kinase activity of the novel human kinase polypeptide described herein is shown in FIG. 6. Lane 1: Novel Kinase+MBP+[γ-$^{32}$P] ATP. Lane 2: Novel Kinase+MBP, no [γ-$^{32}$P] ATP. Lane 3: MBP+[γ-$^{32}$P] ATP, no Novel Kinase. Lane 4: Novel Kinase+[γ-$^{32}$P] ATP, no MBP. Values at left represent molecular weight standards in kDa.

Phosphorylation of MBP (18–20 kDa) and autophosphorylation of the fusion protein kinase (76.9 kDa) are evident in lane 1. No protein phosphorylation was observed when [γ-$^{32}$P] ATP or Novel Kinase were omitted; lane 2 and 3, respectively. Autophosphorylation increased in the absence of the nonspecific substrate (lane 4).

Example III

Production of Anti-kinase Polyclonal Antibodies

Antigenic peptide fragments were identified within the N-terminal, c-terminal and central regions of the novel human kinase utilizing a well established algorithm method developed by Jameson and Wolf. *The Antigenic Index: A Novel Algorithm for Predicting Antigenic Determinants*, CABIOS, 4:181 (1988). The algorithm carries out six major subroutines with the following hierarchy:

1) determination of hydrophilicity, Hopp-Woods (1981)
2) calculation of surface probability, Emini (1985)
3) prediction of backbone or chain flexibility, Karplus-Schultz (1985)
4) prediction of secondary structure, Chou-Fasman (1978)
5) prediction of secondary structure, Garnier-Robson (1978)
6) flexibility parameters and hydropathy/solvent accessibility factors are combined to determine the antigenic index The antigenic index was plotted for the entire molecule. The following peptides were selected for synthesis and antibody production:

1) FKGIDNRTQK SEQ ID NO:3 residues 39–48 (N-terminal)
2) DRNKMKDIPKRP SEQ ID NO:3 residues 348–359 (C-terminal)
3) NNPPTLEGNYSKPL SEQ ID NO:3 residues 234–247 (central)

These peptides were conjugated to keyhole limpet hemocyanin using the IMJECT® Immunogen EDC Conjugation Kit (Pierce). Each conjugated peptide was used to immunize two rabbits according to standard protocols (Harlow and Lane, 1988).

A 165 amino acid peptide from a likely non-catalytic region of the kinase (SEQ ID NO:3 residues 267–432) was PCR cloned and expressed in bacteria from pGEX-5X (Pharmacia) as a GST fusion protein. The purified, unconjugated peptide was used to immunize rabbits as described supra. Chou, P. Y. and Fasman, G. D., (1978) Prediction of the secondary structure of proteins from their amino acid sequence, *Adv. Enzyimol*, 47:45–148; Emini, E. A., Hughes, J., Perlow, D. and Boger, J., (1985) Induction of Hepatitis A Virus-Neutralizing Antibody by a Virus-Specific Synthetic Peptide, *J. Virology*, 55:836–839; Garnier, J., Osguthorpe, D. J., and Robson, B., (1978) Analysis of the accuracy and implications of simple method for predicting the secondary structure of globular proteins, *J. Mol. Biol.*, 120:97–120; Harlow, E. and Lane, D., (1988) Antibodies: A Laboratory Manual., Cold Spring Harbor Laboratory Press, Cold Spring Harbor, N.Y.; Hopp, T. P. and Woods, K. R., (1981) Prediction of Protein Antigenic Determinants from Amino Acid Sequences, *Proc. Natl. Acad. Sci.*, 78:3824–3828; Jameson, B. A., and Wolf, H., (1988) The antigenic index: a novel algorithm for predicting antigenic determinants, *CABIOS* 4:181–186; Karplus, P. A. and Schultz, G. E., (1985) Prediction of chain flexibility in proteins, *Naturwissenschaften*, 72:212–213.

Example IV

Immunoprecipitation

Immunoprecipitation of the human kinase molecule described herein is performed substantially according to the method described by Suchard, S. J., et al. *J. Immunol.*, 158:4961 (1997). Cell lysates are combined with 1 μg of either anti-enterokinase protease cleavage site/Xpress™ antibody (Invitrogen Corp.) for the recombinant kinase described herein or peptide-specific polyclonal antibody against the native kinase described herein. Rabbit IgG is used as a control. Samples are incubated at 4° C. ≧2 hours with rotation. Immunocomplexes are incubated with protein A Sepharose (Pharmacia) for 2 hours at 4° C. with rotation. The beads are washed in buffer containing 50 mM Tris (pH 8.0), 100 mM NaCl, 1 mM Na$_3$VO$_4$, 1% Triton X-100, and Complete™ Protease Inhibitor Cocktail. Adsorbed proteins are solubilized in sample buffer and separated on 12% SDS-PAGE minigels.

Example V

Northern Blot Analysis

Figure 9:
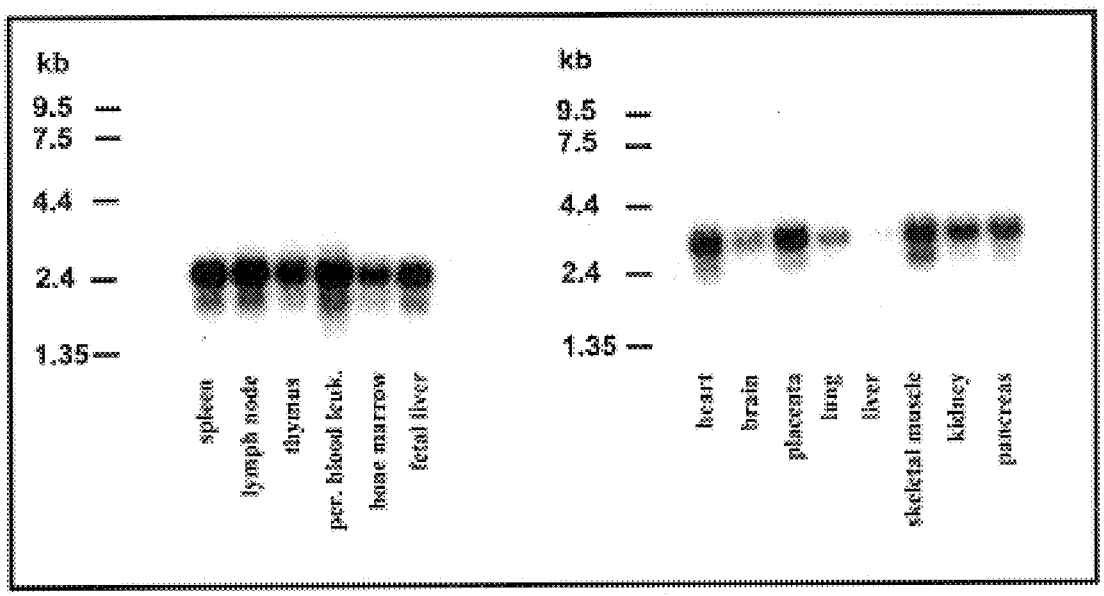
FIG. 9 displays a Northern blot which identifies a primary transcript pertaining to the novel human kinase, approximately 2.5 kilobases in length.

A 784 bp amplicon from the novel human kinase cDNA (SEQ ID NO:1 base positions 128–911) was used as the hybridization probe against CLONTECH Human Immune System Multiple Tissue Northern Blot II and Human Multiple Tissue Northern Blot as sources for poly A+ RNA. Labeling of the probe was performed using the Ready-To-Go™ DNA Labelling Kit (Pharmacia) with 50 μCi [α-$^{32}$P] dATP. Hybridization was performed substantially as described by Clontech (Protocol #PT-1200-1) using ExpressHyb™ hybridization solution. FIG. 9 displays a Northern analysis which identifies a primary transcript pertaining to the novel human kinase, approximately 2.5 kilobases in length. Prominent transcripts are apparent, especially in immune tissues, heart, and skeletal muscle.

Example VI

High Throughput Screening for Compounds which Modulate Activity

High throughput screening for modulator compounds is performed using MBP coated 96-well FlashPlates® (NEN™ Life Science Products). Kinase reaction buffer (3×kinase reaction buffer (KRB) contains: 60 mM HEPES (pH 7.5), 30 mM magnesium acetate, 0.15 mM ATP, 3 mM DTT, 0.03 mM sodium orthovanadate) 0.25 μCi [γ$^{33}$P]-ATP at a concentration no greater than 1 μg/ml, (determined by titration of individual enzyme preparations for a concentration that allows kinetic determinations over a 1 hour time course of the human kinase) are added to each well and incubated 1 hour at 30° C. in the presence or absence of 10 μM test compound. Total reaction volume is 100 μL. Following incubation, the reaction mixture is aspirated and the wells rinsed 2 times with 300 μL PBS. Incorporation of raiolabeled phosphate is determined by scintillation counting, Packard Instrument Co.TopCount, 12-detector, 96-well microplate scintillation counter and luminescence counter, model B991200. Compounds which inhibit kinase activity ≧50 percent at 10 μM are are indicated by a >50% reduction in scintillation counts. Specificity and selectivity studies is determined by titration of inhibitory compounds to determine the IC$_{50}$ (or other standard quantitation well known in the art for comparison) and by the substitution of other kinases in the assay. For example, determination of relative inhibitory activity of the kinase in comparison to recombinant SOK-1, expressed and isolated in a similar manner, assayed under similar conditions, provides selectivity data.

Example VII

High Throughput Screening Protocol

Test Compounds

Test compounds are prepared in advance from 2.5 mg/ml stock solutions in DMSO by diluting 1:10 in distilled water and then 1:10 again. Ten (10)μl of the 1:100 dilution solutions (25 μg/ml in 1% DMSO) are prepared in 96 well Microlite 1 plates (Dynatech) and plates are stored at −20° C. until the evening prior to the start of the assay.

Control Plates

A plate containing control solutions is included in each run of the screen for QA purposes. Such plates are prepared at the beginning of the HTS campaign and stored at −20° C. until required. Zero inhibition (MAX. signal) wells (columns 3, 6, 8 and 10) contain 10 μl of 1% (v/v) DMSO solution in MilliQ water. 100% inhibition (MIN signal) wells (columns 1, 4, 9 and 11) contain 10 μl of 220 nM ZM333141/1 in 1% DMSO solution in MilliQ water. 50% inhibition (REF. signal) wells (columns 2, 5, 7 and 12) contain a reference compound at a concentration known to provide approximately 50% inhibition in 1% (v/v) DMSO solution in MilliQ water.

Assay Components (1) recombinant kinase (expressed in *E. coli* or eukaryotic cells as described herein) or a lysate of a prokaryotic or eukaryotic cell expressing recombinant enzyme, or the natural enzyme partially purified from a human cell line.

(2) [γ-$^{33}$-P]-adenosine triphosphate (3) myelin basic protein linked to the surface of PVT SPA beads (purchased from Amersham International) by an antibody-protein A or other appropriate method.

To Microlite I plates containing 10 μl of test compound, which have been left on the bench overnight to reach room temperature, 25 ml of GST-Rb/ATP/ATP$^{33}$ is added, immediately followed by 20 μl of Enzyme, using two Multidrops. The plates are stacked in 13 plate stacks (with an empty plate on top of each stack to minimise evaporation from the top plate) and left at room temperature for 105 minutes. 150 μl of "Stop Solution" containing beads antibody and EDTA is added using a Multidrop. The plates are sealed with Topseal-S plate sealers and left on the bench overnight, surrounded by Scotlab perspex screens. The plates are then centrifuged (Heraeus Megafuge 3.0R) at 2500 rpm, 1124×g., for 5 minutes (2 plates per trunnion) and counted on a Topcount (I4.34); (isotope:P$^{33}$; counting time: 20 seconds/well).

The data may be analysed using well-known software systems. A threshold for inhibition is set, e.g., 60% inhibition of scintillation signal. Compounds reaching the inhibition threshold are scored as active.

Example VIII

PCR of SEQ ID NO:1 from Various Human cDNAS of Hematopoietic Origin

SEQ ID NO:1 message is determined to be present in other cells of hematopoietic orign by PCR with cDNA's isolated from different cell-lines of hematopoietic orign.

Target product was amplified from 2–2.5 ng of reverse transcribed mRNAs in a 20 μL reaction using Advantage™ KlenTaq polymerase (Clontech #8417-1, lot 7020348) according to the manufacturer's recommendations. Primer set 1 sequences are: 5' CTGAAACACCGGAAGCTC 3' (forward, corresponding to SEQ ID NO:1 nucleotides 1462–1479) and 5' ATGAGGGTATGCAGAGTGG 3' (reverse, corresponding to SEQ ID NO:1 nucleotides 1904–1922). Primer set 2 was the same set used to generate probe for the cDNA library screening. Primer set 2 reactions included DMSO at a final concentration of 5%. Cycling parameters were according to Clontech Marathon-Ready cDNA User Manual (PT1156-1) p. 19, program 1 (briefly, touchdown PCR with 1.5–2 minute extensions). 10 μL of each reaction was analyzed on a 1% agarose gel containing 0.5 μg/mL final concentration ethidium bromide in TAE buffer as in Sambrook et al., Molecular Cloning Lab Manual, Second Edition, Cold Spring Harbor Press (1989), using 600 ng of 1 kb DNA ladder as markers (Life Technologies, cat #15615–016).

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. A purified polynucleotide comprising a nucleotide sequence according to SEQ ID NO:2.

\* \* \* \* \*